United States Patent
North

(10) Patent No.: US 8,415,109 B2
(45) Date of Patent: Apr. 9, 2013

(54) METHODS FOR DIAGNOSING AND TREATING NEUROENDOCRINE CANCER

(75) Inventor: William G. North, Hanover, NH (US)

(73) Assignee: Trustees of Dartmouth College, Hanover, NH (US)

(*) Notice: Subject to any disclaimer, the term of this patent is extended or adjusted under 35 U.S.C. 154(b) by 181 days.

(21) Appl. No.: 12/962,177

(22) Filed: Dec. 7, 2010

(65) Prior Publication Data
US 2011/0086022 A1     Apr. 14, 2011

Related U.S. Application Data

(63) Continuation-in-part of application No. 12/876,312, filed on Sep. 7, 2010, which is a continuation-in-part of application No. 12/254,320, filed on Oct. 20, 2008, now Pat. No. 7,842,468, which is a continuation-in-part of application No. 11/875,067, filed on Oct. 19, 2007, now abandoned, which is a continuation-in-part of application No. PCT/US2006/014660, filed on Apr. 19, 2006.

(60) Provisional application No. 60/672,829, filed on Apr. 19, 2005.

(51) Int. Cl.
*G01N 33/53*     (2006.01)

(52) U.S. Cl. .................................................. 435/7.1

(58) Field of Classification Search ............... None
See application file for complete search history.

(56) References Cited

U.S. PATENT DOCUMENTS

| 6,797,692 B1 | 9/2004 | Ikonomidou | 514/2 |
| 6,896,872 B2 * | 5/2005 | Dambinova | 424/9.1 |
| 7,842,468 B2 * | 11/2010 | North | 435/7.1 |
| 2009/0074764 A1 | 3/2009 | North | 424/133.1 |

FOREIGN PATENT DOCUMENTS

WO PCT/US2011/050519     5/2012

OTHER PUBLICATIONS

Legarza et al (Neuroscience Letters, Jan. 1998, 241(2-3):143-146).*
Kinkelin et al (Neuroscience Letters, 2000, 283: Abstract).*
Dickman et al (AM J Respir Cell Mol Biol, Feb. 2004, 30(2): 139-144).*
Tockman et al (Cancer Res., 1992, 52:2711s-2718s).*
North et al. "NMDA Receptors Are Expressed by Small-cell Lung Cancer and Are Potential Targets for Effective Treatment" Clinical Pharmacology: Advances and Applications 2010 2:31-40.
Choi et al. "The Expression of NMDA Receptor 1 Is Associated with Clinicopathological Parameters and Prognosis in the Oral Squamous Cell Carcinoma" Journal of Oral Pathology & Medicine 2004 vol. 33: 533-537.
Markert et al. "Differential Gene Expression Profiling in Human Brain Tumors" Physiological Genomics 2001 vol. 5: 21-33.
North et al. "Presence of Functional NMDA Receptors in a Human Neuroblastoma Cell Line" Molecular and Chemical Neuropathology 1997 vol. 30: 77-94.
Rzeski et al. "Glutamate Antagonists Limit Tumor Growth" Biochemical Pharmacology 2002 vol. 64: 1195-1200.

* cited by examiner

*Primary Examiner* — Sean Aeder
(74) *Attorney, Agent, or Firm* — Licata & Tyrrell P.C.

(57) ABSTRACT

The present invention relates to a method for diagnosing neuroendocrine cancers via detecting the presence of N-methyl D-asparate-associated (NMDA) glutamate receptors type 1 and/or type 2. Methods for preventing and treating neuroendocrine cancers are also disclosed.

1 Claim, 6 Drawing Sheets

METHODS FOR DIAGNOSING AND TREATING NEUROENDOCRINE CANCER

This application is a continuation-in-part application of U.S. patent application Ser. No. 12/876,312, filed Sep. 7, 2010, which is a continuation-in-part application of U.S. patent application Ser. No. 12/254,320, filed Oct. 20, 2008, now U.S. Pat. No. 7,842,468 which is a continuation-in-part application of U.S. patent application Ser. No. 11/875,067, filed Oct. 19, 2007, now abandoned, which is a continuation-in-part application of PCT/US2006/014660, filed Apr. 19, 2006, which claims benefit of priority to U.S. Provisional Patent Application Ser. No. 60/672,829, filed Apr. 19, 2005, the contents of which are incorporated herein by reference in their entirety.

This invention was made with government support under Grant Nos. CA19613 and CA135428 awarded by the National Cancer Institute and Grant No. DAM D17-94-J-4288 awarded by the Department of Defense. The government has certain rights in the invention.

BACKGROUND OF THE INVENTION

Glutamate is the major excitatory neurotransmitter in central nervous system (CNS) and as such, the glutamate receptors play a vital role in the mediation of excitatory synaptic transmission. The ionotropic receptors themselves are ligand-gated ion channels, i.e., on binding glutamate that has been released from a companion cell, charged ions such as $Na^+$ and $Ca^{2+}$ pass through the receptor complex thereby depolarizing the plasma membrane and generating an electrical current.

The ionotropic glutamate receptors are multimeric assemblies of four or five subunits, and are subdivided into three groups (AMPA, NMDA and Kainate receptors) based on their pharmacology structural similarities. All ionotropic glutamate receptor subunits share a common basic structure. Like other ligand-gated ion channels, such as the $GABA_A$ receptor, the ionotropic glutamate receptor subunits possess four hydrophobic regions within the central portion of the sequence (transmembrane I-IV). However, in contrast to other receptor subunits, the transmembrane II domain forms a re-entrant loop giving these receptor subunits an extracellular N-terminus and intracellular C-terminus. In addition, the long loop between transmembrane III and transmembrane IV, which is intracellular in other ligand-gated ion channel subunits, is exposed to the cell surface, and forms part of the binding domain with the C-terminal half of the N-terminus.

NMDA receptors are composed of assemblies of NMDA Type 1 (NMDAR1) and NMDA Type 2 (NMDAR2) glutamate receptors, which can be one of four separate gene products (NMDAR2 a-d). Expression of both subunits is required to form functional channels. The glutamate binding domain is formed at the junction of NMDAR1 and NMDAR2. In addition to glutamate, the NMDA receptor requires a co-agonist, glycine, to bind to allow the receptor to optimally function. The glycine binding site is found on the NMDAR2 and NMDAR2b also possesses a binding site for polyamines, regulatory molecules that modulate the functioning of the NMDA receptor.

North et al. ((1997) *Mol. Chem. Neuropathol.* 30(1-2):77-94) teach the expression of structurally normal and functional NMDA receptors by acetylcholine-producing human LA-N-2 neuroblastoma cells in culture. Cell cytotoxicity was shown by a neutral red cytotoxicity assay to be increased through incubation with glutamate at 1 and 10 mM by 27 and 37%, and through incubation with NPG at 0.1 and 1 mM by 28 and 46%. Further, a voltage-dependent tetrodotoxin-sensitive inward sodium current was found to be increased (×1.5) by L-glutamic acid and by ACDA and NPG NMDA agonists in the presence of glycine. It was concluded that the glutamate activities observed in human LA-N2 neuroblastoma cells appeared to occur through the activation of functional NMDA receptors in much the same way as reported for neurons, and both glutamate and NMDA agonists can be toxic to these neuroblastoma cells.

Rzeski et al. ((2002) *Biochem. Pharmacol.* 64:1195-200) teach the influence of glutamate antagonists on the proliferation and migration of tumor cells. This reference teaches that glutamate N-methyl-D-aspartate (NMDA) and alpha-amino-3-hydroxy-5-methyl-4-isoxazole-propionate (AMPA) antagonists inhibit the proliferation of human colon adenocarcinoma, astrocytoma, breast and non-small cell lung carcinoma, and neuroblastoma cells in vitro. The antiproliferative effect of glutamate antagonists is $Ca^{+2}$-dependent and results from decreased cell division and increased cell death. Glutamate antagonists produce morphological alterations in tumor cells, which consist of reduced membrane ruffling and pseudopodial protrusions, and decrease their motility and invasive growth. Furthermore, glutamate antagonists enhance in vitro cytostatic and cytotoxic effects of common chemotherapeutic agents used in cancer therapy.

Choi et al. ((2004) *J. Oral Pathol. Med.* 33(9):533-7) disclose that immunohistochemical staining for NMDAR1 was positive in 50 of 81 oral squamous cell carcinoma (OSCC) cases, while it was negative in the control. NMDAR1 expression was significantly associated with a lymph node metastasis (P=0.008), the tumor size (P<0.001), and the cancer stage (P=0.034). The patients whose tumors expressed NMDAR1 had a significantly poorer survival than the patients who were NMDAR1-negative.

U.S. Pat. No. 6,797,692 teaches a method for treating cancer (e.g., a cell exhibiting abnormal or uncontrolled cell growth with resulting invasion and destruction of neighboring tissue). The method involves administering an inhibitor of the interaction between glutamate with a glutamate receptor complex (i.e., AMPA, KA or NMDA receptor complexes).

SUMMARY OF THE INVENTION

The present invention is a method for diagnosing a neuroendocrine cancer. The method involves the steps of isolating a sample from a patient and detecting the presence of at least one NMDA glutamate receptor, or nucleic acids encoding the same, in said sample wherein the presence of at least one NMDA glutamate receptor, or nucleic acids encoding the same, is indicative of said patient having or at risk of having a neuroendocrine cancer.

The present invention is also a method for decreasing proliferation of a neuroendocrine tumor cell. This method involves contacting a neuroendocrine tumor cell with an effective amount of an agent which inhibits or decreases the activity or expression of an NMDA glutamate receptor thereby decreasing proliferation of the neuroendocrine tumor cell.

The present invention is further a method for preventing or treating a neuroendocrine cancer in a subject. This method includes administering to a subject having or at risk of having a neuroendocrine cancer an effective amount of an agent which inhibits or decreases the activity or expression of an NMDA glutamate receptor thereby preventing or treating a neuroendocrine cancer in the subject.

BRIEF DESCRIPTION OF THE DRAWINGS

FIG. 1 shows the effect of memantine on NCI-H345 and NCI-H82 cell proliferation.

FIG. 2 shows the effect of MK-801 on NCI-H345 and NCI-H82 cell proliferation.

FIG. 3 shows the effect of Ifenprodil on NCI-H345 and NCI-H82 cell proliferation.

DETAILED DESCRIPTION OF THE INVENTION

Figure 1A:
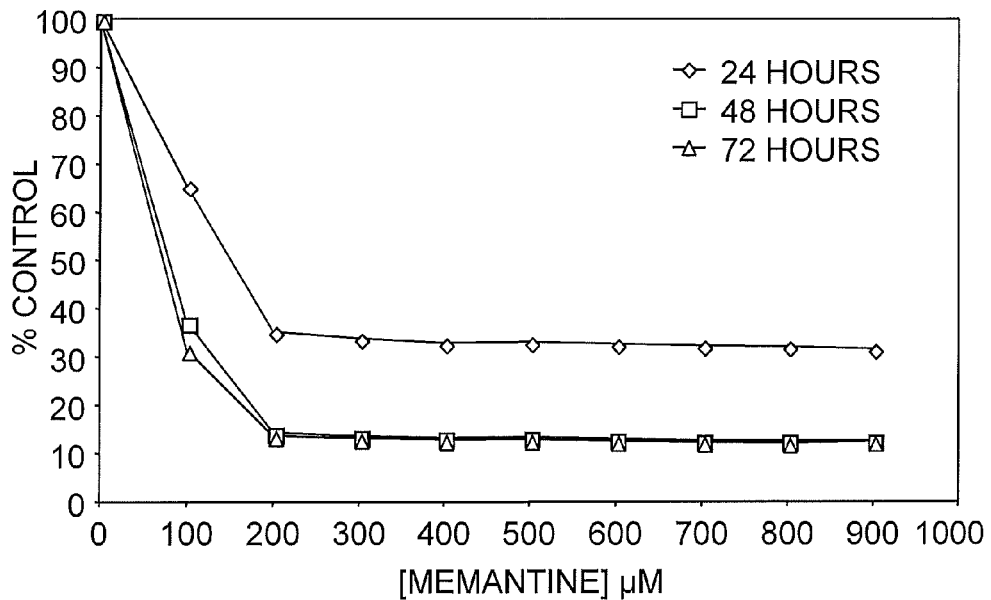
FIG. 1A shows the percentage reduction in cell viability produced in NCI-H345 classical cells by the action of irreversible NMDAR1 receptor antagonist memantine following 24, 48, and 72 hours incubation.

The present invention relates to the use of N-methyl D-asparate-associated (NMDA) glutamate receptors for diagnosing neuroendocrine tumors as well as targets for the prevention or treatment of neuroendocrine tumors. An NMDA glutamate receptor, as used in the context of the present invention, is intended to include NMDA Type 1 (i.e., NMDAR1) and NMDA Type 2 (i.e., NMDAR2abcd) glutamate receptors.

As used herein, a neuroendocrine cancer or tumor is either one which arises from the neuroendocrine system, a diffuse system in which the nervous system and the hormones of the endocrine glands interact, or from non-endocrine cells by acquiring some of the properties of neuroendocrine cells through an oncogenic process such as Selective Tumour gene Expression of Peptides essential for Survival (STEPS) (see, North (2000) *Exper. Physiol.* 85S:27S-40S). Most of the well-described adult neuroendocrine tumors are distinctive and arise from a known primary site, including the carcinoid, pheochromocytoma, and Merkel's cell tumors. Carcinoid tumors can be benign or malignant. Carcinoid cancers include stomach, pancreas, colon, liver, lung, ovarian, breast, testicular, and cervical cancer. Neuroendocrine tumors of the lungs are classified as small cell carcinoma. It is characterized by its origin in large central airways and histological composition of sheets of small cells with scanty cytoplasm. Small cell carcinoma is very aggressive, metastasizing early and often. Pheochromocytoma is a cancer of the adrenal medulla. This condition often causes the adrenal glands to make too much catecholamine. Pheochromocytoma may arise as part of a condition called multiple endocrine neoplasia (MEN) syndrome, which can result in other cancers of the endocrine system and hormonal abnormalities. Merkel's cell tumors are cancers that form on or just beneath the skin, but sometimes are also thought to arise from underlying soft tissue. They are also known as neuroendocrine cancer of the skin. Merkel's cell tumors are fast-growing and often spread to other parts of the body. In particular embodiments of the present invention, a neuroendocrine cancer is a carcinoid cancer such as breast cancer or SCLC.

The results presented herein indicate that neuroendocrine tumor cells express both NMDAR1 and NMDAR2 glutamate receptors, whereas normal cells from these same tissues lack NMDAR1 and NMDAR2 expression. Accordingly, the present invention is a method for diagnosing a neuroendocrine cancer in a patient suspected of having or at risk of having a neuroendocrine tumor by detecting the presence of at least one NMDA glutamate receptor. The method involves isolating a sample from the patient and detecting the presence of at least one NMDA glutamate receptor, or nucleic acids encoding the same, in the sample. In one embodiment, the assay of the present invention is carried out by detecting the presence of NMDAR1 or NMDAR2. In another embodiment, the assay of the present invention is carried out by detecting the presence of both NMDAR1 and NMDAR2. In particular embodiments pertaining to NMDAR2, one or both of NMDAR2A and NMDAR2B are detected. As used in the context of the present invention, a sample is intended to mean any bodily fluid or tissue which is amenable to protein or nucleic acid analysis. Suitable samples which can be analyzed in accordance with the method of the present invention include, but are not limited to, sputum, vaginal or rectal swabs, biopsy samples, and the like isolated from a patient (e.g., human, livestock or companion animal) according to standard clinical practices. It is contemplated that the sample can be from an individual suspected of having a neuroendocrine tumor or from an individual at risk of having a neuroendocrine tumor, e.g., an individual in remission or having a family history which predisposes the individual to neuroendocrine cancer.

In one embodiment of this diagnostic method, the presence of at least one NMDA glutamate receptor is detected in assays using a binding agent which specifically binds to a NMDA glutamate receptor protein (i.e., NDMAR1 and/or NMDAR2) and no other ionotropic glutamate receptor (e.g., AMPA or Kainate receptors). In this embodiment, a sample is contacted with a binding agent (e.g., antibody), which binds an NMDA glutamate receptor, and the resulting receptor-binding agent complex is detected using standard assays (e.g., an immunoassay). When the binding agent is, for example, a peptide aptamer, the receptor-binding agent complex can be directly detected by, for example, a detectable marker protein (e.g., β-galactosidase, GFP or luciferase) fused to the aptamer. Subsequently, the presence or absence of the receptor-binding agent complex is correlated with the presence or absence, respectively, of a neuroendocrine tumor cells in the sample and therefore the presence or absence, respectively, of a neuroendocrine cancer in the patient. It is contemplated that one or more binding agents of the present invention can be used in conjunction with current non-invasive immuno-based imaging techniques (e.g., mammography) to greatly enhance detection and early diagnosis of neuroendocrine tumors. For example, as SCLC is currently diagnosed on the basis of gross morphological and histological data obtained from biopsied tissue and is often identified after the disease has reached its advanced stages, the instant method can be used for early diagnosis of SCLC. Additionally, ductal carcinoma in situ (DCIS) is often difficult to discern from atypical ductal hyperplasia (ADH), generally considered to be a benign affliction, on biopsied tissue sections. These biopsied tissue samples could be stained using binding agents disclosed herein, allowing for differential diagnoses to be made thereby improving subsequent treatment procedures and outcomes.

Binding agents for use in accordance with the instant invention include antibodies, as well as peptide aptamers. In particular embodiments of the present invention, the binding agent specifically recognizes at least a portion of the N-terminal extracellular domain of at least one NMDA glutamate receptor (i.e., NMDAR1 or NMDAR2). The extracellular domain of an NMDAR1 receptor can be found at about amino acid residues 19-560 of GENBANK Accession number Q05586 (Planells-Cases, et al. (1993) *Proc. Natl. Acad. Sci. USA* 90:5057-5061). Likewise, the extracellular domain of NMDAR2 receptors A, B, C, and D can be found at about amino acid residues 23-28 to 555-583 of GENBANK Accession numbers NP_000824 (Monyer, et al. (1992) *Science* 256(5060):1217-21), NP_000825 (Monyer, et al. (1992) supra), NP_000826 Monyer, et al. (1992) supra) and NP_000827 (Hess, et al. (1998) *J. Neurochem.* 70(3):1269-79), respectively. A particularly suitable antigenic fragment of the extracellular domain of NMDAR1 for generating antibodies to NMDAR1 is Met-Ser-Ile-Tyr-Ser-Asp-Lys-Ser-Ile-His (SEQ ID NO:5). Other suitable antigenic regions of the extracellular domain of these proteins can be readily identified by the skilled artisan using any art-established computer algorithm for identifying such antigenic sequences (e.g., Jamison and Wolf (1988) *Bioinformatics* 4:181-186; Carmenes, et al. (1989) *Biochem Biophys Res Commun.* 159(2): 687-93). To generate a binding agent specific for all isoforms of NMDAR2, it is desirable that an antigenic peptide common to all isoforms be used to generate the binding agent. In one embodiment, the binding agent is specific for at least a portion of the extracellular domain of NMDAR2A, NMDAR2B, NMDAR2C, or NMDAR2D. In another embodiment, the binding agent is specific for at least a portion of the extracellular domain of all isoforms of NMDAR2 (i.e., A, B, C, and D).

Antibodies to an NMDA glutamate receptor can be generated using methods that are well-known in the art. Such antibodies can include, but are not be limited to, polyclonal, monoclonal, chimeric, single chain, Fab fragments, bispecific scFv fragments, Fd fragments and fragments produced by a Fab expression library.

For the production of antibodies, various hosts including goats, rabbits, rats, mice, humans, and others, may be immunized by injection with an NMDA glutamate receptor protein or any fragment or oligopeptide thereof which has antigenic or immunogenic properties. An exemplary fragment is the N-terminal extracellular domain of an NMDA glutamate receptor (i.e., SEQ ID NO:5). Depending on the host species, various adjuvants can be used to increase the immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are particularly suitable.

An antibody to an NMDA glutamate receptor can be generated by immunizing an animal with an oligopeptide, peptide, or fragment, e.g., of the N-terminal extracellular domain of the NMDA glutamate receptor protein. Generally, such oligopeptides, peptides, or fragments have an amino acid sequence consisting of at least five amino acids and more desirably at least 10 amino acids. Fragments of an NMDA glutamate receptor protein can be generated by, for example, tryptic digestion and extraction from a preparative SDS-PAGE gel or by recombinant fragment expression and purification. Further, short stretches of amino acids of an NMDA glutamate receptor antigen of the invention can be fused with those of another protein such as keyhole limpet hemocyanin and antibody produced against the chimeric molecule.

Monoclonal antibodies to an NMDA glutamate receptor protein of the invention can be prepared using any technique which provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256:495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell. Biol.* 62:109-120).

In addition, techniques developed for the production of humanized and chimeric antibodies, the splicing of mouse antibody genes to human antibody genes to obtain a molecule with appropriate antigen specificity and biological activity, can be used (Morrison, et al. (1984) *Proc. Natl. Acad. Sci.* 81, 6851-6855; Neuberger, et al. (1984) *Nature* 312:604-608; Takeda, et al. (1985) *Nature* 314:452-454). Alternatively, techniques described for the production of single chain antibodies can be adapted, using methods known in the art, to produce specific single chain antibodies. Antibodies with related specificity, but of distinct idiotypic composition, can be generated by chain shuffling from random combinatorial immunoglobulin libraries (Burton (1991) *Proc. Natl. Acad. Sci.* 88:11120-11123).

Antibodies can also be produced by inducing in vivo production in the lymphocyte population or by screening immunoglobulin libraries or panels of highly specific binding reagents as is well-known in the art (Orlandi, et al. (1989) *Proc. Natl. Acad. Sci.* 86: 3833-3837; Winter, et al. (1991) *Nature* 349:293-299).

Antibody fragments, which contain specific binding sites for an NMDA glutamate receptor protein, or a fragment thereof, can also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed to allow rapid and easy identification of monoclonal Fab fragments with the desired specificity (Huse, et al. (1989) *Science* 254:1275-1281).

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger et al. (1993) *Proc. Natl. Acad. Sci. USA* 90:6444; Poljak (1994) *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, as for example described by Holliger, et al. (1993) supra, Poljak (1994) supra, Zhu, et al. (1996) *Biotechnology* 14:192-196, and U.S. Pat. No. 6,492,123, herein incorporated by reference, can be used.

Various immunoassays can be used for screening to identify antibodies, or fragments thereof, having the desired specificity for NMDA glutamate receptor antigen. Numerous protocols for competitive binding (e.g, ELISA), latex agglutination assays, immunoradiometric assays, and kinetics (e.g., BIACORE™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. Such assays can also be used in the detection of an NMDA glutamate receptor in a sample.

Peptide aptamers which specifically bind to an NMDA glutamate receptor protein can be rationally designed or screened for in a library of aptamers (e.g., provided by Aptanomics SA, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range). Likewise, aptamers which bind to nucleic acid sequences encoding an NMDA glutamate receptor protein can also be identified in library screens.

A binding agent can also be subjected to other biological activity assays, e.g., cancer cell growth assays, in order to evaluate its potency or pharmacological activity and potential efficacy as a therapeutic agent. Such assays are described herein and are well-known in the art.

In an alternate embodiment of the diagnostic method of the present invention, the presence of the NMDA glutamate receptor protein in a sample (e.g., samples provided supra) is detected via the presence of nucleic acid sequences encoding an NMDA glutamate receptor. Nucleic acid sequences encoding an NMDA glutamate receptor can be detected using any well-known method including, but not limited to, northern blot analysis, reverse-transcriptase PCR, PCR, microarray, and the like. Due to the ease of use, it is generally desirable to detect the nucleic acid sequences using a PCR-based approach. In general, this involves contacting the sample with two or more PCR primers which specifically hybridize with nucleic acids encoding an NMDA glutamate receptor or which flank the coding region of an NMDA glutamate receptor, subjecting the sample to multiple steps of PCR amplification and detecting the presence or absence of the amplified sequence (e.g., using gel analysis, blotting methods, or fluorescently-labeled primers). Alternatively, an oligonucleotide, an aptamer, a cDNA, an antibody, or a fragment thereof, which interacts with at least a portion of the nucleic acid encoding an NMDA glutamate receptor protein is configured in an array on a chip or wafer and used for detecting nucleic acids encoding an NMDA glutamate receptor. Briefly, these techniques involve methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11):5022-6; Fodor, et al. (1991) *Science* 251(4995):767-73).

Primers or oligonucleotides for use in this embodiment can be selected from any region of the locus encoding an NMDA glutamate receptor protein and generally specifically anneal and amplify at least a portion of a nucleic acid encoding an NMDA glutamate receptor and no other nucleic acid encoding a closely related protein. Suitable primers for amplification of nucleic acids encoding NMDAR1 include those exemplified herein (e.g., SEQ ID NO:1, SEQ ID NO:2, SEQ ID NO:3, and SEQ ID NO:4) or can be selected by the skilled artisan from the nucleic acid sequences encoding NMDAR1 (i.e., GRIN1) disclosed in Foldes, et al. (1993) *Gene* 131:293-298); Zimmer, et al. (1995) *Gene* 159:219-223), or Foldes, et al. (1994) *Gene* 147:303-304. See also GENBANK Accession Nos. NM_000832, NM_021569, and NM_007327. Suitable primers for amplification of nucleic acids encoding NMDAR2 A-D can likewise be selected by the skilled artisan from the nucleic acid sequences encoding NMDAR2 A-D (i.e., GRIN2A-D) disclosed in Monyer, et al. (1992) supra or Hess, et al. (1998) supra. See also GENBANK Accession Nos. NM_000833, NM_000834, NM_000835, and NM_000836. Exemplary primers for NMDAR2B are set forth herein in SEQ ID NO:6, SEQ ID NO:7, SEQ ID NO:8, and SEQ ID NO:9, whereas exemplary primers for NMDAR2A are set forth in SEQ ID NO:10 and SEQ ID NO:11.

In general, suitable primers are 12 to 30 bp in length and generate a PCR amplicon of 50, 100, 200, 400, 600, 1000 bp or more in length. In accordance with this method, a geometrically amplified product is obtained only when the first and second nucleotide sequences occur within the same nucleic acid molecule encoding the NMDR glutamate receptor protein. The fundamentals of non-degenerate PCR are well-known to the skilled artisan, see, e.g. McPherson, et al., PCR, A Practical Approach, IRL Press, Oxford, Eng. (1991).

Typically, the diagnostic method of the present invention will include a positive and/or negative control to assess the accuracy of the method.

In conjunction with the diagnostic method of the present invention, a kit for identifying the presence of an NMDA glutamate receptor protein is also provided. A kit of the invention includes a container containing at least one binding agent (e.g., an antibody) which specifically binds a NMDA glutamate receptor protein. Alternatively, the kit contains suitable primers (e.g., those disclosed herein) for amplifying nucleic acids encoding at least one NMDA glutamate receptor. The kit can also contain other solutions necessary or convenient for carrying out the invention. The container can be made of glass, plastic or foil and can be a vial, bottle, pouch, tube, bag, etc. The kit may also contain written information, such as procedures for carrying out the present invention or analytical information, such as the amount of reagent contained in the first container means. The container can be in another container, e.g., a box or a bag, along with the written information.

As further demonstrated herein the NMDAR1 and NMDAR2 glutamate receptors are fully functional in the cancer cells, and that the function of these receptors is to influence the growth and viability of cancer cells/tumors. Accordingly, the present invention is also a method for decreasing or inhibiting the proliferation of a neuroendocrine tumor cell (e.g., in vitro or in vivo cells or cell lines of neuroendocrine tumors disclosed herein) using an agent which inhibits or decreases the activity or expression of an NMDA glutamate receptor. As used herein, an agent which inhibits or decreases the activity of an NMDA glutamate receptor is intended to include binding agents (e.g., antibodies or peptide aptamers as disclosed herein), antagonists, partial antagonists and the like which have the effect of blocking the ability of the NMDA glutamate receptor to bind modulatory compounds (e.g., glutamate, glycine, or polyamines) or block the channel pore thereby decreasing the activity of the NMDA glutamate receptor. An agent which inhibits or decreases the expression of an NMDA glutamate receptor is intended to include small molecules or nucleic acids which hybridize with nucleic acids coding for an NMDA glutamate receptor and inhibit or decrease the expression thereof.

Antagonists useful in accordance with the methods of the present invention include antagonists which act at the glutamate binding site of NMDA glutamate receptors. Exemplary antagonists of this type include, but are not limited to, L-glutamate derivatives, (R)-2-amino-5-phosphonopentanoate, (R)-(E)-4-(3-phosphonoprop-2-enyl)piperazine-2-carboxylic acid, (±)-cis-4-(4-phenylbenzoyl)piperazine-2,3-dicarboxylic acid and the like.

Antagonism of the glycine binding site will also antagonize NMDA receptor function. A series of high affinity antagonists have been developed for this binding site on the NMDA receptor and include, but are not limited to, L-701,324; L-689,560; and GV96771A, which displace glycine binding with affinities below 10 nM.

The effects of polyamine site antagonists are specific for channels containing the NR2B subunit. Hence, a polyamine site antagonist which would be useful as an NR2B antagonist for this site includes, but is not limited to, Ro 25-6981.

Channel blockers refer to compounds that bind to the pore of the NMDA receptor channel and block transport of cations (e.g., $Na^+$, $K^+$ and $Ca^{2+}$ ions). NMDA receptor channel blockers useful in accordance with the methods of the present invention include, e.g., magnesium, dizocilpine (MK801), phencyclidine, ketamine, memantine, tiletamine, budipine, flupirtine, 1-[1-(2-thienyl)cyclohexyl]piperidine (TCP), and (+)-(3S,4S)-7-hydroxy-delta6-tetrahydrocannabinol-1,1-dimethylheptyl (HU211).

Glutamate-related agonists are further contemplated. High levels of glutamate-related agonists in the presence of glycine were found to be cytotoxic to neuroendocrine tumor cells in vitro. Suitable glutamate-related agonists for use in accordance with the methods of the present invention, include, but are not limited to, homoquinolinic acid, NPG and ACDA.

In particular embodiments of the instant methods, an agent that inhibits or reduces the activity of an NMDA glutamate receptor is a binding agent which binds to at least a portion of the N-terminal extracellular domain of NMDAR1 or NMDAR2. Such binding agents include antibodies, antibody fragments and peptide aptamers as disclosed supra. Antibodies of use in the instant invention include, but are not limited to, polyclonal antibodies, monoclonal antibodies, diabodies, bispecific antibodies, humanized antibodies, affinity matured antibodies and conventional fragments thereof.

Agents useful for decreasing the expression on an NMDA glutamate receptor include agents having a sequence complementary to at least part of NMDA glutamate receptor nucleic acid sequence. Without being limited by theory, the inhibition of expression by the agent is achieved through selective hybridization with NMDA glutamate receptor DNA or mRNA thereby impeding any steps in the replication, transcription, splicing or translation of a NMDA glutamate receptor nucleic acid. Examples of agents that can be used decrease expression of an NMDA glutamate receptor include, but are not limited to, antisense oligonucleotides, ribozymes, nucleic acids molecules that promote triple helix formation, and siRNAs (or shRNA) or co-repression of a target gene by introducing a homologous gene fragment into the cell that harbors the target gene.

A sequence is complementary when it hybridizes to its target sequence under high stringency, i.e., conditions for hybridization and washing under which nucleotide sequences, which are at least 60 percent (preferably greater than about 70, 80, or 90 percent) identical to each other, typically remain hybridized to each other. Such stringent conditions are known to those skilled in the art, and can be found, for example, in Current Protocols in Molecular Biology, John Wiley & Sons, N.Y. (1989), 6.3.1-6.3.6. Another example of stringent hybridization conditions is hybridization of the nucleotide sequences in 6× sodium chloride/sodium citrate (SSC) at about 45° C., followed by 0.2×SSC, 0.1% SDS at 50-65° C. Another example of stringent hybridization conditions is hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Alternatively, a stringent hybridization condition is hybridization in 6× sodium chloride/sodium citrate (SSC) at about 45° C., followed by one or more washes in 0.2×SSC, 0.1% SDS at 65° C. Another alternative example of stringent hybridization condition is 0.5 M sodium phosphate, 7% SDS at 65° C., followed by one or more washes at 0.2×SSC, 1% SDS at 65° C.

Antisense nucleotide sequences that can be used to decrease or inhibit the expression of an NMDA glutamate receptor include nucleotide sequences that are complementary to the nucleotide sequences including, but are not limited to, GENBANK accession numbers NM_000832, NM_021569, NM_007327, NM_000833, NM_000834, NM_000835, and NM_000836 or paralogs or orthologs, or portions thereof.

Further, an antisense nucleotide sequence can be designed that is specific for an alternatively spliced variant of an NMDA glutamate receptor by directing the antisense nucleotide sequence to nucleic acid sequences specific to the variant of interest. A particularly suitable NMDA glutamate receptor-specific antisense oligonucleotide is disclosed in Weyermann et al. ((2004) J. Control. Release. 100(3):411-23).

Those skilled in the art can appreciate that it is not necessary that the antisense nucleotide sequence be fully complementary to the target sequence as long as the degree of sequence similarity is sufficient for the antisense nucleotide sequence to hybridize to its target and reduce production of NMDA glutamate receptor protein (e.g., by at least about 40%, 50%, 60%, 70%, 80%, 90%, 95% or more). As is known in the art, a higher degree of sequence similarity is generally required for short antisense nucleotide sequences, whereas a greater degree of mismatched bases will be tolerated by longer antisense nucleotide sequences.

Alternatively stated, antisense nucleotide sequences should have at least about 60%, 70%, 80%, 90%, 95%, 97%, 98% or higher sequence similarity with the complement of the NMDA glutamate receptor coding sequences to reduce the level of NMDA glutamate receptor production.

The length of the antisense nucleotide sequence is not critical as long as it binds selectively to the intended location and reduces transcription and/or translation of the target sequence. In general, the antisense nucleotide sequence will be from about eight, ten or twelve nucleotides in length up to about 20, 30, 50, 60 or 70 nucleotides, or longer, in length.

In another embodiment, RNA interference (RNAi) is used to modulate NMDA glutamate receptor expression. RNAi has proven successful in human cells, including human embryonic kidney and HeLa cells (see, e.g., Elbashir, et al. (2001) *Nature* 411:494-8). The mechanism by which RNAi achieves gene silencing has been reviewed in Sharp, et al. (2001) *Genes Dev* 15:485-490; and Hammond, et al. (2001) *Nature Rev. Gen.* 2:110-119). Accordingly, NMDA glutamate receptor expression can be inhibited by introducing into or generating within a cell (i.e., transgenic expression) an RNAi molecule that targets an NMDA glutamate receptor-encoding nucleic acid or fragment thereof. In certain embodiments the RNAi molecule is a siRNA, a shRNA, an encapsulated RNA, a double stranded RNA, or other molecule capable of generating RNA interference, or combinations thereof. Methods for inhibiting NMDA glutamate receptor expression via RNAi can entail the direct administration of an siRNA or siRNA-like molecule into a cell, or use of the vector-based methods (e.g., an shRNA encoded by a lentiviral vector). In one embodiment, the RNAi molecule is less than about 30 nucleotides in length. In a further embodiment, the RNAi molecule is about 21-23 nucleotides in length. In another embodiment, an siRNA molecule is a 19-21 bp duplex, each strand having a two nucleotide 3' overhang. Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art.

Silencing effects similar to those produced by RNAi have been reported in mammalian cells with transfection of a mRNA-cDNA hybrid construct (Lin, et al. (2001) *Biochem. Biophys. Res. Commun.* 281:639-44), providing yet another strategy for silencing a coding sequence of interest.

In a further embodiment, the agent can further be a ribozyme. Ribozyme catalysis has primarily been observed as part of sequence-specific cleavage/ligation reactions involving nucleic acids (Joyce (1989) *Nature* 338:217). For example, U.S. Pat. No. 5,354,855 reports that certain ribozymes can act as endonucleases with sequence specificities greater than that of known ribonucleases and approaching that of the DNA restriction enzymes. Thus, sequence-specific ribozyme-mediated inhibition of gene expression may be particularly suited to therapeutic applications (Scanlon, et al. (1991) *Proc. Natl. Acad. Sci. USA* 88:10591; Sarver, et al. (1990) *Science* 247:1222; Sioud, et al. (1992) *J. Mol. Biol.* 223:831).

As will be appreciated by the skilled artisan, stable oligonucleotide analogs can also be used for inhibiting or reducing expression of an NMDA glutamate receptor. Such analogs can have the negatively charged sugar-phosphate backbone replaced by a polypeptide backbone leading to enhanced stability and the formation of stronger hybrids with complementary RNA and DNA. Likewise 2'-sugar modifications are also contemplated.

Neuroendocrine tumor cell proliferation is decreased or inhibited by contacting tumor cells with an effective amount of one or more of the agents disclosed herein which inhibit or decrease the activity or expression of an NMDA glutamate receptor. Desirably, the agent decreases the neuroendocrine tumor cell proliferation by about 10%, 20%, 30%, 40%, 50%, 60%, 70%, 80%, 90% or 100% as compared to the same cell in the absence of the agent; an effect which can be determined in accordance with standard methods for measuring rates of cell proliferation.

By inhibiting or decreasing neuroendocrine tumor cell proliferation, this method of the present invention will be useful as a research tool for studying the signaling pathways involved in the growth and development of neuroendocrine tumors and for preventing or treating neuroendocrine tumors in vivo.

Therefore, the present invention is also a method for preventing or treating a neuroendocrine cancer in a subject by administering to a subject having or at risk of having a neuroendocrine cancer an effective amount of an agent which inhibits or decreases the activity or expression of an NMDA glutamate receptor. Prevention or treatment typically involves the steps of first identifying a subject having or at risk of having a neuroendocrine cancer. Individuals having cancer generally refers to subjects who have been diagnosed with neuroendocrine cancer and require treatment, whereas individuals at risk of having a neuroendocrine cancer may have a family history of such a cancer or exhibit one or more signs or symptoms associated with such a cancer and require prevention of the same. Once such a subject is identified using, for example, standard clinical practices, the subject is administered a pharmaceutical composition containing an effective amount of an agent which inhibits or decreases the activity or expression of an NMDA glutamate receptor (e.g., agents disclosed supra). In most cases, the subject being treated will be a human being, but treatment of agricultural animals, e.g., livestock and poultry, and companion animals, e.g., dogs, cats and horses, is expressly covered herein.

In particular embodiments of the instant method, an agent that inhibits or decreases the activity of an NMDA glutamate receptor is a binding agent that binds to at least a portion of the N-terminal extracellular domain of NMDAR1 or NMDAR2. Such binding agents include antibodies, antibody fragments and peptide aptamers as disclosed supra. Advantageously, binding agents such as antibodies and antibody fragments will not generally cross the blood-brain barrier and bind to NMDA glutamate receptors located in central neurons. Therefore, side-effects associated with inactivation of neuronal NMDA glutamate receptors will be minimized.

The selection of the dosage or effective amount of the agent is that which has the desired outcome of reducing or reversing at least one sign or symptom of neuroendocrine cancer. For example, depending on the cancer, some of the general signs or symptoms can include a tumor, increased pain perception, weakness, abdominal pain, anemia, pneumonia, a cough, and spitting of blood.

For therapeutic use, the agent is generally formulated with a pharmaceutically acceptable vehicle, such as water, buffered saline, polyol (for example, glycerol, propylene glycol, liquid polyethylene glycol and the like) or suitable mixtures thereof. The optimum concentration of the active ingredient(s) in the chosen vehicle can be determined empirically, according to procedures well-known to medicinal chemists. As used herein, pharmaceutically acceptable vehicle includes any solvent, dispersion medium, and the like which may be appropriate for the desired route of administration of the pharmaceutical preparation. The use of such vehicle for pharmaceutically active substances is known in the art. Suitable vehicles and their formulation inclusive of other proteins are described, for example, in Remington: The Science and Practice of Pharmacy, Alfonso R. Gennaro, editor, 20th ed. Lippingcott Williams & Wilkins: Philadelphia, Pa., 2000.

A pharmaceutical composition containing an agent (e.g., a binding agent or antisense oligonucleotide) which blocks NMDA glutamate receptor activity or expression and a pharmaceutically acceptable vehicle can be used alone or in combination with other well-established agents useful for preventing or treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, pulmonary delivery may be advantageously used over subcutaneous delivery for the treatment of SCLC. Local or systemic delivery can be accomplished by application or instillation of the formulation into body cavities; inhalation or insufflation of an aerosol; or by parenteral introduction, including intramuscular, intravenous, intraportal, intrahepatic, peritoneal, subcutaneous, or intradermal administration.

Those of ordinary skill in the art can readily optimize effective doses and co-administration regimens as determined by good medical practice and the clinical condition of the individual patient. Regardless of the manner of administration, it can be appreciated that the actual preferred amounts of active agent in a specific case will vary according to the particular formulation and the route of administration. The specific dose for a particular patient depends on age, body weight, general state of health, on diet, on the timing and route of administration, on the rate of excretion, and on medicaments used in combination and the severity of the particular disorder to which the therapy is applied. Dosages for a given subject can be determined using conventional considerations, e.g., by customary comparison of the differential activities of the selected agent and of a known agent, such as by means of an appropriate conventional pharmacological protocol. By way of illustration, dosing of an antibody raised against at least a portion of the N-terminal extracellular domain of NMDAR1 or NMDAR2 can be based upon dosing of antibodies such as HERCEPTIN® (Trastuzumab) and ERBITUX® (Cetuximab or IMC-C225) currently used in the treatment of breast cancer and colorectal cancer, respectively.

In addition to being directly useful in the prevention and treatment of neuroendocrine cancers, the binding agents of the present invention are also useful as cell-surface targeting moieties as they have been shown to specifically bind to neuroendocrine tumor cells and not normal cells. A cell-surface targeting moiety is defined as an agent which specifically targets a chemotherapeutic, therapeutic, radiotherapeutic or in situ imaging agent to a neuroendocrine cancer cell.

Chemotherapy and therapeutic anticancer agents which will be used in conjunction with a neuroendocrine cancer targeting moiety of the invention include, cytotoxic agents such as Taxol, Cytochalasin B, Gramicidin D, Ethidium Bromide, Emetine, Mitomycin, Etoposide, Tenoposide, Vincristine, Vinblastine, camptothecin (CPT), Colchicin, Doxorubicin, Daunorubicin, Mitoxantrone, Mithramycin, Actinomycin D, 1-Dehydrotestosterone, Glucocorticoids, Procaine, Tetracaine, Lidocaine, Propranolol, blocked ricin (Lynch, et al. (1997) *J. Clin. Oncol.* 15(2):723-34) and Puromycin and analogs or homologs thereof. Therapeutic agents include, but are not limited to, antimetabolites (e.g., methotrexate, 6-mercaptopurine, 6-thioguanine, cytarabine, 5-fluorouracil, decarbazine), alkylating agents (e.g., mechlorethamine, thiotepa, chlorambucil, melphalan, carmustine, lomustine, cyclophosphamide, busulfan, dibromomannitol, streptozotocin, mitomycin C, cis-dichlorodiamine platinum (II), cisplatin), anthracyclines (e.g., daunorubicin and doxorubicin), antibiotics (e.g., dactinomycin, bleomycin, mithramycin, and anthramycin), anti-mitotic agents (e.g., vincristine and vinblastine) and selective apoptotic agents such as APTOSYN® (exisulind), PANZEN™ (2-methoxyestradiol), and VELCADE® (bortezomib). Radiotherapeutic agents which can be targeted to neuroendocrine tumors via binding agents are well-known in the art. See, e.g., Ballangrud, et al. (2004) *Clin. Cancer Res.* 10(13):4489-97. NMDA glutamate receptor binding agents can also advantageously be used to target NMDA glutamate receptor agonists or antagonists to NMDA glutamate receptors located on neuroendocrine tumor cells as such binding agents should not cross the blood-brain barrier.

The use of an NMDA glutamate receptor as a neuroendocrine tumor antigen for vaccinating a subject having or at risk of having a neuroendocrine tumor is also expressly contemplated herein. A vaccine can include an isolated NMDA glutamate receptor, or an antigenic fragment thereof, and a pharmaceutically acceptable vehicle. Using art-established methods, an isolated NMDA glutamate receptor protein or antigenic fragment can be recombinantly-produced, chemically-synthesized, or isolated from cells which naturally express an NMDA glutamate receptor. Alternatively, nucleic acid encoding an NMDA glutamate receptor protein or antigenic fragment can be part of a viral-based vaccine. One or more amino acids, not corresponding to the original protein sequence can be added to the amino or carboxyl terminus of the original peptide, or truncated form of peptide. Such extra amino acids are useful for coupling the protein to another peptide, to a large carrier protein, or to a support which can enhance the immunological response to the vaccine. Amino acids that are useful for these purposes include: tyrosine, lysine, glutamic acid, aspartic acid, cysteine and derivatives thereof. Alternative protein modification techniques can be used, e.g., $NH_2$-acetylation or COOH-terminal amidation, to provide additional means for coupling or fusing the protein/peptide to another protein or peptide molecule or to a support. Active immunization can be induced by administering one or more antigenic and/or immunogenic epitopes of an NMDA glutamate receptor protein as a component of a vaccine. Vaccination can be performed orally, nasally or parenterally in amounts sufficient to enable the recipient to generate protective antibodies against this biologically functional region, prophylactically or therapeutically. In addition to a pharmaceutically acceptable vehicle, the NMDA glutamate receptor antigen, or antigenic fragment thereof, can be co-administered with an adjuvant to enhance the immunological response to the vaccine. During et al. ((2000) *Science* 287 (5457):1453-60) teach a particularly suitable adeno-associated virus (AAV) vaccine for generating autoantibodies to NMDAR1. The single-dose vaccine disclosed was well-tolerated and able to produce a neuroprotective activity in rats. Such a vaccine will be useful as an immuno-based approach to tumor eradication and prevention.

The invention is described in greater detail by the following non-limiting examples.

Example 1

Materials and Methods

Cell Culture. Breast cancer (i.e., MCF-7 and SKBR3) and SCLC (i.e., classical human SCLC cell lines NCI-H345, DMS-53, NCI-H146, and the variant SCLC cell line, NCI-H82), cells were maintained at 37° C. in an atmosphere of 5% $CO_2$ using Dulbecco's Minimal Essential Medium (DMEM; 0.8 mM $Mg^{2+}$, 0.4 mM glycine; Sigma, St. Louis, Mo.) or RPMI 1640 (Mediatech, Inc., Herndon, Va.) supplemented with 10% fetal bovine serum and 50 µg/mL gentamicin. Every 3-4 days, cells received fresh DMEM or were subcultured using 0.06% trypsin with 0.02% EDTA. Cell densities were at $10^5$ to $5 \times 10^5$/ml.

MCF-7 and SKBR3 are art-established cell cultures for analyzing the pathophysiology of breast cancer and preclinical analysis of drug efficacy (Hanauske (2004) *Oncology (Huntingt)*. 18(13 Suppl 8):66-9). In particular, studies using MCF-7 cultures have correlated well with in vivo therapeutic studies. For example, Johnson, et al. ((1997) *Semin Oncol.* 24(1 Suppl 3):S22-5) teach that paclitaxel and 5-fluorouracil have additive cytotoxicity in MCF-7 cell lines and is an active, well-tolerated regimen in metastatic breast cancer.

RNA Isolation, RT-PCR and Northern Blot Analysis. Poly (A)$^+$ RNA was isolated from cells using oligo(dT) cellulose chromatography in accordance with well-established methods (Badley, et al. (1988) *Biotechniques* 5:114-116).

For RT-PCR, Poly(A)$^+$ RNA (2 µg) from breast cancer or SCLC cells was denatured at 70° C. for 10 minutes and chilled on ice. First strand cDNA synthesis was carried with a SUPERSCRIPT™ preamplification system (GIBCO-BRL®, Gaithersburg, Md.), using an oligo(dT) primer and 1 µL (200 U) of SUPERSCRIPT™ II reverse transcriptase (PROMEGA®, Madison, Wis.). The reverse transcriptase product was directly used as a template for the PCR reaction. PCR was carried out using GENEAMP® PCR reagents (PERKIN ELMER™, Foster City, Calif.) in a thermocycler (EASY CYCLER™ Series, ERICOMP, San Diego, Calif.). The templates were initially denatured at 97° C. for 8 minutes and amplified for 30 cycles under the following conditions: denaturation at 95° C. for 30 seconds; annealing at 58° C. for 1.5 minutes; and extension at 72° C. for 1.5 minutes. After the cycling reaction was complete, an additional extension step was carried out at 72° C. for 10 minutes. Primers used in the amplification of the NMDAR1 receptor included F1, 5'-ATC TAC TCG GAC AAG AGC ATC C-3' (SEQ ID NO:1, corresponding to nucleotides 369 to 417 of the sequence set forth in GENBANK Accession No. L05666); R1,5'-AGC TCT TTC GCC TCC ATC AG-3' (SEQ ID NO:2, corresponding to compliment nucleotides 658 to 639 of GENBANK Accession No. L05666); F2,5'-AAG TAT GCG GAT GGG GTG ACT-3' (SEQ ID NO:3, nucleotides 1002 to 1022 of GENBANK Accession No. L05666); R2,5'-CAA AAG CCG TAG CAA CAC TGA-3' (SEQ ID NO:4, nucleotides 1393 to 1373 of GENBANK Accession No. L05666). NMDAR2B primers included forward primer 1,5'-TCA AGG ATG CCC ACG AGA AAG-3' (SEQ ID NO:6, corresponding to nucleotide residues 358 to 378 of GENBANK Accession No. NM_000834); reverse primer 1,5'-GTG GCT TCT TCC TTG TGA CAG-3 (SEQ ID NO:7, corresponding to nucleotide residues 922 to 902 of GENBANK Accession No. NM_000834); forward primer 2,5'-CCA AAG AGC ATC ATC ACC C-3' (SEQ ID NO:8, corresponding to nucleotide residues 441 to 459 of GENBANK Accession No. NM_000834); reverse primer 2,5'-TGT AGC CAT AGC CAG TCA G-3' (SEQ ID NO:9, corresponding to nucleotide residues 972 to 954 of GENBANK Accession No. NM_000834). NMDAR2A primers included forward primer, 5'-TCC AAT AGT GCC CTG CTA AG-3' (SEQ ID NO:10) and reverse primer, 5'-TGC CAA CAT ACC CAG TAG GC-3' (SEQ ID NO:11), which amplify a 220 base pair fragment corresponding to nucleotides 4780-4999 of GENBANK Accession No. NM_000833.2 (human GRIN2A). These primers were synthesized by a commercial source. The PCR products were purified by washing once with an equal volume of chloroform and examined on 2% agarose gels. DNase-free RNase and RNase-free DNase (GIBCO/BRL) were employed in some reactions to validate that the products of PCR did not result from initial DNA contamination.

To confirm that the amplicons encoded the correct NMDAR protein, they were cloned into PCR™ vector and transformed into ONE SHOT™ Competent Cells using a TA CLONING® kit (INVITROGEN™, San Diego, Calif.). At least two clones of each amplicon were selected for double-stranded cDNA sequencing with a TAQ DYEDEOXY™ Terminator Cycle Sequencing Kit (APPLIED BIOSYSTEMS™, Foster City, Calif.). F1, F2, R1 and R2 primers in combination with universal primers M13 Forward, M13 reverse, and T7 were used as sequencing primers. The protocol for DNA amplification was modified as follows: 97° C., 2 minutes; 25 cycles of 95° C., 30 seconds; 58° C., 1.5 minutes; and 72° C., 1.5 minutes with a 72° C. extension for 10 minutes. Amplicons were purified and sequencing was performed using Model 373 DNA Sequencer (APPLIED BIOSYSTEMS™, Foster City, Calif.). Upon BLAST analysis, it was determined that the amplicon for NMDAR1 coded for a segment of the N-terminal extracellular domain of NMDAR1 which was nearly identical in sequence to NMDAR1 from human neurons.

Northern Blot Analysis. Northern blot analysis was performed with 10 µg of poly(A)$^+$ RNA from breast cancer and SCLC cells. RNA was denatured and fractionated on a 1.2% formaldehyde agarose gel. Separated products were transferred to nitrocellulose membranes (NITRO-PURE™; MSI, Westboro, Mass.) with 10×SSC transfer buffer, vacuum-dried for 2 hours, and prehybridized at 42° C. for 4 hours. PCR amplicons were radiolabeled with [$^{32}$P]dCTP (3000 Ci/mmol; DUPONT®/NEN, Boston, Mass.) using the DECAPRIME II™ DNA labeling kit (Ambion, Inc., Austin, Tex.) and used to hybridize with the membrane at 42° C. for 18 hours. The membrane was washed twice at room temperature, first in a 2×SSC solution containing 0.1% SDS and then in a 0.1×SSC solution containing 0.1% SDS. The membrane was subsequently washed twice under stringent conditions of 55° C. in 0.1×SSC containing 0.1×SSC and exposed to X-ray film for 5 to 7 days.

PANN1 is a rabbit polyclonal antiserum produced against an N-terminal segment of NMDAR1. Antibodies from this antiserum were first isolated by affinity chromatography. Commercially available NMDAR1 antiserum was obtained from Cell Signaling, and NMDAR2 antiserum was purchased from Santa Cruz (NMDAe2, Santa Cruz Biochemicals, Santa Cruz, Calif.). The latter antiserum recognizes all NMDAR2 subunits. After analysis with anti-NMDAR antibodies, the blots were stripped and incubated with GAPDH (Chemicon), or scanned with anti-β-actin (SIGMA), to ensure equal protein loading.

Neutral Red Assay. Breast cancer and SCLC cells were subcultured into 24-well plates (CORNING®, Corning, N.Y.). After 24 hours, the growth medium was aspirated and replaced with growth medium containing L-glutamic acid (Sigma, St. Louis, Mo.) at concentrations of 0, 1, or 10 mM, or N-phthaloyl-L-glutamic acid (NPG; Research Biochemicals Inc., Natick, Mass.) at concentrations of 0, 0.1 or 1 mM. Following 48 hours of incubation at 37° C., the experimental medium was removed and replaced with DMEM containing 40 μg/mL neutral red (Sigma, St. Louis, Mo.). After a two hour incubation, the neutral red was aspirated and the cell monolayers carefully washed with phosphate-buffered saline (PBS). Incorporated dye was extracted from cells with 50% ethanol/1% acetic acid. The absorbance of recovered dye was determined at 540 nm or fluorescence measured at excitation of 530 nm and emission 650 nm.

Immunocytochemistry. Samples, i.e., cancer cell lines or cancer tissue isolated from patients, were trypsinized and plated into chamber slides (Nunc, Naperville, Ill.). Subsequently, the samples were washed with PBS, blocked with 1.5% goat serum for 30 minutes, and fixed in acetone for 2 minutes. Samples were washed with PBS and stained for about 1 hour at room temperature with either rabbit polyclonal antiserum raised against a NMDAR1 peptide of SEQ ID NO:5 or rabbit polyclonal antiserum raised against NMDAR2abcd (Santa Cruz Biochemicals, Santa Cruz, Calif.) in PBS containing 10% normal goat serum (GIBCO-BRL®, Gaithersburg, Md.). Samples were then washed with PBS and incubated for 30 minutes with biotinylated goat anti-rabbit IgG (Vector Labs, Burlingame, Calif.). Samples were subsequently washed with PBS and incubated with avidin-peroxidase complex for 30 minutes. Visualization of the antigen-antibody complex was performed by the peroxidase oxidation of 3,3'-diaminobenzidine. A negative control incubated with 1.5% goat-serum instead of primary antibody confirmed that staining was not as a result of non-specific reactivity of the secondary antibody.

Cell Growth/Viability Assay. Cultures of NCI-H345, NCI-H146, DMS-53 cells (classical cell lines), and NCI-H82 cells (variant cell line) were treated with 0.05% trypsin, washed in phosphate buffered saline (PBS)/glycine and plated onto 96-well plates at $10^4$ cells/well in medium for 24 hours to provide time for rectifying possible damage to membrane proteins from the trypsinization. The wells were washed and incubated with PBS/glycine containing albumin (1.25 mg/mL) in the presence or absence of different concentrations (25 μM-800 μM) of either the NMDAR 1 antagonists, Memantine or MK-801; or the NMDAR2B antagonists Ifenprodil and Ro 25-6981 (binders to the polyamine site), or the NMDAR2B antagonists L-701,252 and L-701,324 (binders to the glycine site), or vehicle; and Alamar Blue (1:10 dilution following manufacturer's recommendation). Fluorescent readings were taken at periods representing 24, 48, and 72 hours of incubation with antagonist using a Synergy HT Multi-Detection Microplate Reader and excitation/emission wavelengths of 530 nm and 590 nm. Cell viability was evaluated as % vehicle control at the corresponding incubation time.

Rabbit polyclonal anti-NMDAR1 antibodies (PANN1) were generated against an N-terminal extracellular peptide domain (Met-Ser-Ile-Tyr-Ser-Asp-Lys-Ser-Ile-His (SEQ ID NO:5)) of the human receptor, in the form of the peptide amide coupled through glutaraldehyde to bovine thyroglobulin as antigen, and use of Fruend's complete and incomplete adjuvant (Friedmann, et al. (1994) *Br. J. Cancer* 69:260-263; Keegan, et al. (2002) *Mol. Cancer. Therapeutics.* 1:1153-1159). This peptide domain is represented in that portion of the mRNA message sequenced by RT-PCR. For studies on cell proliferation, the IgGs of this antiserum were first isolated by precipitation with 50% saturated ammonium sulfate, and antibodies purified from these immunoglobulins by affinity chromatography using a column containing the peptide component of the above antigen coupled to SEPHAROSE (Friedmann, et al. (1994) supra; Keegan, et al. (2002) supra). Two dilutions (1/10 and 1/50) of an affinity-purified PANN1 antibody preparation in PBS/0.5% BSA (<<375 fmol Ab and <<75 fmol Ab) were incubated with cells in 1640 medium for 24 hours at 37° C., and cell growth compared with cells treated with liquid vehicle using the Alamar Blue procedure.

Treatment of SCLC Tumor Xenografts in Mice. Human tumor xenografts of small cell lung cancer (SCLC) cell line NCI-H345 were raised in nu/nu mice, and the influence of the NMDAR1 receptor antagonist dizocilpine maleate (MK-801) then examined on established tumor growth measured by multiplying depth, width, and length determined using a micrometer. Tumor growth in a control group of animals receiving i.p. PBS vehicle (n=4) was compared to tumor growth in animals (n=4) receiving dizocilpine maleate (MK-801) over 10 days. Animals received an escalating single dose of this NMDAR1 antagonist from 0.1 mg/Kg body weight each day for days 0-2, then to a single dose of 0.2 mg/Kg body weight each day for days 3-6, then to a single dose of 0.3 mg/Kg body weight each day for days 7-8. Finally two daily doses of 0.3 mg/Kg body weight were given for days 8-10.

Results were analyzed by Analysis of Variance and the Student-Neuman-Kuels test. Longitudinal growth data was evaluated using repeated measures ANOVA. Significant was determined to be present for $p<0.05$.

Example 2

NMDAR1 and NMDAR2 Expression in Cancer Cells

SCLC. Analysis of the expression of the NMDA receptors by cultured SCLC cells and tumor tissues was carried out using RT-PCR of poly($A^+$)RNA preparations. All four SCLC cell lines tested (NCI-H345, DMS-53, NCI-H146 and NCI-H82) yielded in each case, a single overlapping product of size predicted from the structure of cDNA for human NMDAR1 from brain tissue, and reported for human LA-N-2 neuroblastoma cells (North, et al. (1997) *Mol. Chem. Neuropath.* 30:77-94). Cloning and nucleotide sequence analysis of these NMDA glutamate receptor RT-PCR products (488 bp and 263 bp), coding for portions of the extracellular domain, showed them to have exact sequence homology with position 208-695 of the brain and neuroblastoma receptor, and sequence identity in this portion of the NMDAR1 receptor for all four SCLC cell lines. The region in the mRNA examined represents approximately 30% of the open reading frame for the extracellular N-terminal domain for this receptor subunit. As was found for the mRNA from LA-N-2 cells, there was no evidence for alternate splicing of the message as has been reported for NMDAR1 from rat brain (Moriyoshi, et al. (1991) *Nature* 354:31-37). RT-PCR of poly($A^+$) RNA was unaffected by prior treatment of preparations with DNase, and no products were generated when initial treatment with RNase was performed or when reverse transcriptase was omitted from reaction mixtures. Nucleotide sequencing also revealed normal sequences for the two other regions of NMDAR1 mRNA amplified giving predicted RT-PCR products of 300 and 391 nucleotides. In addition, RT-PCR of NMDAR2B message provided predicted products of 471 and 564 nucleotides, that upon nucleotide sequencing were shown to have sequences identical to those known in the art (Hess, et al. (1996) *J. Pharmacol. Exper. Therap.* 278:808-816). Likewise, real-time RT-PCR analysis of NMDAR2A indicated that the small-cell lung cancer cell lines NCI H345, NCI H146, and DMS 53 (all representing primary disease) and NCI H82 (representing recurrent disease) expressed this receptor.

There is a consensus that the molecular weight of the NMDAR1 protein subunit is 116 kDaltons, and a major band of approximately this size was displayed for NCI-H345, NCI-H82, NCI-146, and DMS-53 cells in western analysis using affinity-purified PANN1 antibodies. A second minor band of approximately 55 kD was also apparent. This second band could be an N-terminal break-down product of the receptor, because PANN1 is directed against an N-terminal moiety of the protein. Alternatively, the NMDAR2 subunits are 165-180 kDaltons, and a major band of approximately 170 kDaltons (in addition to bands corresponding to smaller proteins) was displayed in western blots of all SCLC cell lines by the NMDAR2e polyclonal antibody employed (i.e., an antibody that recognizes the extracellular domain of NMDAR2B), indicating that NMDAR2A, B, or C of normal size is expressed by all of the cell lines. Further, the NMDAR2e polyclonal antibody indicated the presence of one or more of these proteins in two breast cancer cell lines (i.e., MCF-7 and SKBR3). Indeed, RT-PCR analyses confirmed the presence of the NMDAR1 and NMDAR2A transcripts in the MCF-7 and SKBr3 breast cancer cell lines. Coupled with RT-PCR data, it was concluded that SCLC and breast cancer cells express and translate NMDAR1 receptor as well as NMDAR2B and NMDAR2A forms of the NMDAR2 receptor.

Immunohistochemical evaluation of SCLC tumor sections with anti-NMDAR1 antibodies gave strong and clear positive staining for eight of ten tumors, and weak, questionable staining in the other two cases examined. All of the 6 cases of metastatic and recurrent disease were among those giving a strong positive reaction. Normal cells in each section did not react with the antibodies. No positive staining of normal lung and liver was apparent with PANN1 anti-NMDAR1 antibodies for the same conditions of IHC, except for Kufper cells in the liver and isolated macrophages in both tissues.

Breast Cancer. Similarly, immunohistochemical analysis of fixed breast cancer tissues indicated that breast cancer tissue expresses NMDAR1, whereas normal breast tissue epithelial or myoepithelial cells do not stain positive for the presence of this receptor.

Ovarian Cancer. Immunohistochemical analysis of an array containing 12 tissue samples, and an additional 10 sections of invasive ovarian cancers (total=22) was performed. The polyclonal antibodies employed in this analysis were generated against a unique peptide region in the extracellular N-terminal domain of the human NMDAR1. This peptide was coupled to bovine thyroglobulin so it could be used as an effective antigen in generating polyclonal antibodies in rabbits. For immunohistochemistry, the active IgG2b fraction of the antiserum was isolated using protein A SEPHAROSE. The sABC technique of immunohistochemistry, with citrate 'antigen recovery', on 4 μm sections was employed (SSI System, Biogenex). Controls included successfully blocking antibody with an excess of peptide antigen. Studies revealed the presence of NMDAR1 in seemingly all neoplastic cells of all tumor tissue microdots and all sections. No staining was found with normal ovary tissues.

NMDA Receptor expression on ovarian cancer cell lines was also evaluated. This analysis demonstrated that NMDARs were present on A2780, OV2008, and SK-0V3 cells as determined by western blot analysis and confocal microscopy employing polyclonal antibodies raised against the extracellular fragment of NMDAR1 described herein. It was of note that when antibodies reacted with the receptors, the receptor-antibody complexes appeared to internalize.

Prostate Cancer. Immunohistochemical of 22 cases of prostate cancer were also analyzed for NMDAR expression. Anti-NMDAR1 antibodies were employed in these studies and were generated against the unique and extracellular N-terminal domain of the receptor. The sABC technique of immunohistochemistry, with citrate 'antigen recovery', on 4 μm sections was employed. Controls included successfully blocking primary antibody with excess of peptide antigen. These studies revealed the presence of NMDAR1 receptors in seemingly all neoplastic cells of all tumor tissue sections analyzed. No staining was found with normal human prostate tissues.

In addition to immunohistochemical analysis, it was found that NMDAR1 receptors were present on LNCAP and PC3 prostate cancer cell as determined by western analysis and by confocal microscopy employing anti-NMDAR polyclonal antibodies. It was of note that when antibodies reacted with the receptors, the receptor-antibody complexes appeared to internalize.

Pancreatic Cancer. Immunohistochemical analysis was performed on an array of 12 cases of invasive pancreatic cancers, with four samples of normal adjacent pancreatic tissue also analyzed. Anti-NMDAR1 antibodies against the unique and extracellular N-terminal domain of the receptor were used as described herein. For immunohistochemistry, the active IgG2b fraction of the antiserum was isolated using protein A SEPHAROSE. The sABC technique of immunohistochemistry, with citrate 'antigen recovery' was employed (SSI System, Biogenex). Controls included successfully blocking antibody with excess of peptide antigen. Studies revealed the presence of NMDAR1 in seemingly all neoplastic cells of all pancreatic tumor tissue microdots. No staining was found in the normal pancreatic tissues.

In addition to immunohistochemical analysis, it was found that NMDARs are present on Panc-1, HPAC-1, and BXCPC-3 cells as determined by western blot analysis and confocal microscopy employing anti-NMDAR polyclonal antibodies to the extracellular fragment of NMDAR1. This analysis showed that intact NMDAR1 of ~120 Kd was expressed by pancreatic cancer cells Panc-1 and BXCPC-3, and that surface fluorescent staining of this receptor was evident. Moreover, it was of note that when antibodies reacted with the receptors, they appeared to internalize.

Example 3

In Vitro Anti-Cancer Activity of NMDAR Antagonists

Breast Cancer and SCLC. Growth and NMDA glutamate receptor activity in cancer cells were found to respond to the effects of glutamate (NMDAR1 agonist) in the presence of glycine (NMDAR2 agonist) over 24 hours. Glutamate decreased cell growth in LAN2 cells, and increased proliferation in breast cancer cells under the conditions used (Table 1, $p<0.05$).

TABLE 1

| | Fluorescence (nm) | |
|---|---|---|
| Cell Line | Vehicle | Agonist |
| LAN2 | 465 | 420 |
| MCF7 | 485 | 510 |
| SKBr3 | 345 | 445 |

Results represent triplicate studies performed with Alamar Blue on LAN2 neuroblastoma, MCF-7 breast cancer, and SKBr3 breast cancer cells examining the growth influence of 1 mM glutamate in the presence of glycine over 24 hours.

Treatment of these cells with magnesium (NMDAR1 antagonist) in the presence of glycine (NMDAR1 agonist)

over 24 hours further indicated functional receptor activity, in that magnesium significantly inhibited proliferation of all cell types (Table 2, p<0.05).

TABLE 2

| Cell Line | Fluorescence (nm) | |
|---|---|---|
| | Vehicle | Antagonist |
| LAN2 | 420 | 150 |
| MCF7 | 800 | 550 |
| SKBrS | 330 | 160 |

Results represent triplicate studies performed with Alamar Blue on LAN2 neuroblastoma, MCF-7 breast cancer, and SKBr3 breast cancer cells examining the growth influence of 100 mM $Mg^{++}$ in the presence of glycine over 24 hours.

Further, it was found an affinity-purified preparation of polyclonal antibody against the N-terminal region (SEQ ID NO:5) of human NMDAR1 (PANN1) when administered at 1:50 (<<10 ng, <<0.075 pmol antibody) or 1:10 (<<50 ng, <<0.38 pmol antibody) could decrease the proliferation of small cell lung cancer H345 cells in culture by about 6% and 25%, respectively, compared to controls (Table 3).

TABLE 3

| Treatment | Fluorescence (nm) | | |
|---|---|---|---|
| | 24 Hours | 48 Hours | 72 Hours |
| Control, 1:50 | 723.5 ± 3.8 | 789.2 ± 13.1 | 610.7 ± 4.1 |
| PANN1, 1:50 | 678.0 ± 2.8** | 784.3 ± 7.1 | 605.8 ± 3.8 |
| Control, 1:10 | 811.3 ± 5.5 | 927.2 ± 8.2 | 596.5 ± 3.7 |
| PANN1, 1:10 | 617.0 ± 2.9** | 665.5 ± 7.4** | 507.0 ± 2.2** |

**p < 0.001. Fluorescence due to Alamar Blue is a linear representation of proliferation.

Moreover, treatment with NMDAR1 antagonist, MK801, was found to decrease proliferation of SKBr3 and MCF-7 breast cancer cells. For example, a concentration of 0.9 mM reduced proliferation of SKBr3 cells at 72 hours by about 80% (Table 4).

TABLE 4

| MK801 (μM) | Proliferation of SKBr3 Cells Percent Fluorescence Compared to Control | | |
|---|---|---|---|
| | 24 Hours | 48 Hours | 72 Hours |
| 100 | 92.29 ± 6.82 | 91.74 ± 2.94 | 95.06 ± 1.22 |
| 200 | 89.47 ± 5.77 | 89.35 ± 2.83 | 93.24 ± 1.68 |
| 300 | 84.39 ± 5.01 | 83.79 ± 2.71 | 88.97 ± 2.04 |
| 400 | 75.17 ± 4.67 | 70.62 ± 2.34 | 77.08 ± 2.78 |
| 500 | 65.50 ± 3.74 | 59.07 ± 2.49 | 67.02 ± 5.13 |
| 600 | 58.06 ± 3.00 | 50.59 ± 2.34 | 52.57 ± 2.28 |
| 700 | 51.97 ± 2.77 | 43.84 ± 3.41 | 44.88 ± 3.40 |
| 800 | 43.27 ± 2.50 | 33.77 ± 4.19 | 33.91 ± 4.35 |
| 900 | 35.73 ± 2.66 | 25.48 ± 5.92 | 25.21 ± 5.96 |

Likewise, NMDAR1 antagonist memantine decreased the proliferation of MCF-7 and SKBr3 breast cancer cells. For example, concentration of 0.3 mM was found to reduce proliferation of MCF-7 cells at 48 and 72 hours by about 80% (Table 5).

TABLE 5

| Memantine (μM) | Proliferation of MCF-7 Cells Percent Fluorescence Compared to Control | | |
|---|---|---|---|
| | 24 Hours | 48 Hours | 72 Hours |
| 100 | 92.86 ± 6.08 | 89.98 ± 5.30 | 88.48 ± 4.02 |
| 200 | 73.51 ± 5.64 | 49.78 ± 6.85 | 46.62 ± 7.04 |
| 300 | 48.81 ± 5.18 | 22.33 ± 5.21 | 20.02 ± 4.97 |
| 400 | 39.62 ± 5.21 | 15.79 ± 4.79 | 14.38 ± 3.92 |
| 500 | 38.40 ± 2.98 | 14.60 ± 3.21 | 13.40 ± 3.29 |
| 600 | 39.22 ± 4.13 | 15.10 ± 7.28 | 13.66 ± 6.62 |
| 700 | 32.80 ± 2.19 | 12.51 ± 2.35 | 11.89 ± 2.62 |
| 800 | 32.82 ± 2.44 | 12.34 ± 2.01 | 11.82 ± 2.25 |
| 900 | 32.23 ± 2.13 | 12.03 ± 2.15 | 11.57 ± 2.41 |

Figure 1B:
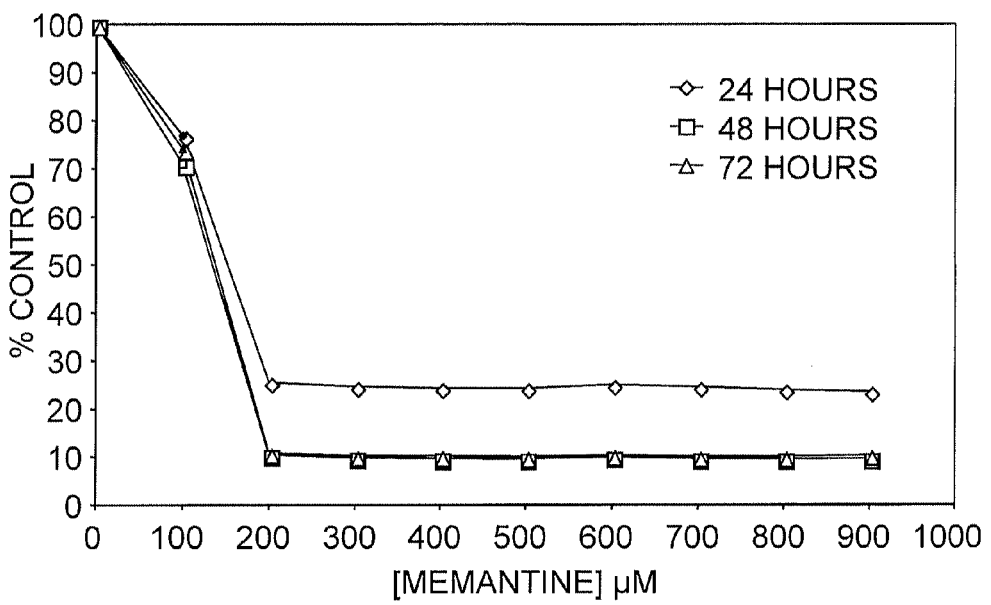
FIG. 1B shows the percentage reduction in cell viability produced in NCI-H82 variant cells by the action of irreversible NMDAR1 receptor antagonist memantine following 24, 48, and 72 hours incubation. Cell viability was reduced to about 10% of control and assessed using Alamar Blue staining. Reductions in viability were highly significant ($p<0.0001$) and $IC_{50}$s were obtained with 80-100 µM doses of antagonist at 48 and 72 hours of incubation.
Figure 2A:
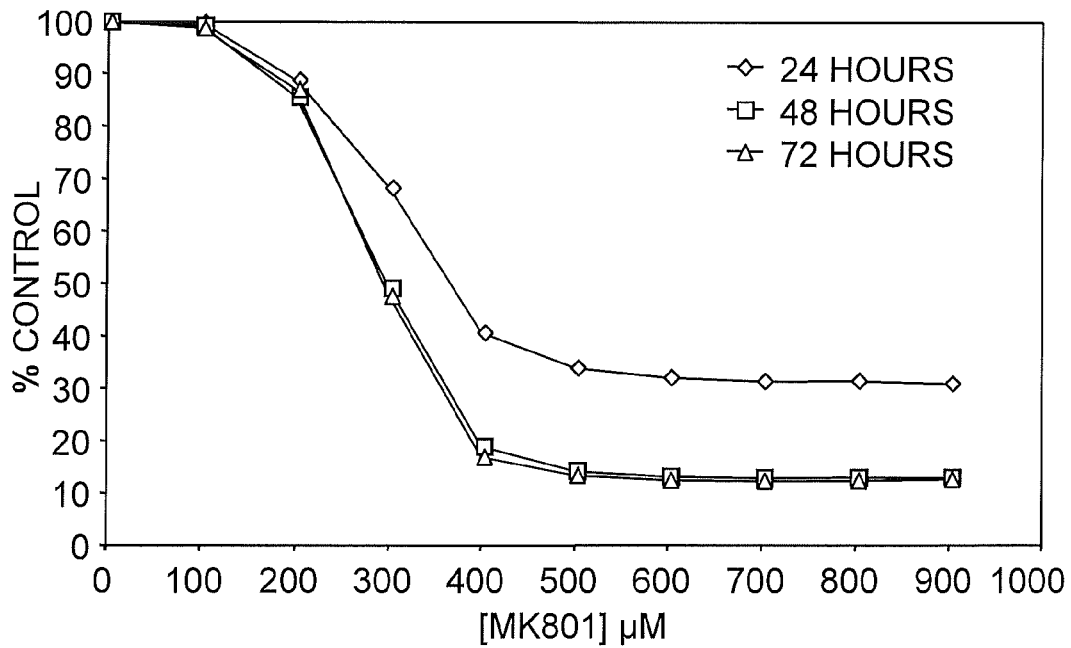
FIG. 2A shows the percentage reduction in cell viability produced in NCI-H345 classical cells by the action of irreversible NMDAR1 receptor antagonist MK-801 (dizocilpine maleate) following 24, 48, and 72 hours of incubation.
Figure 2B:
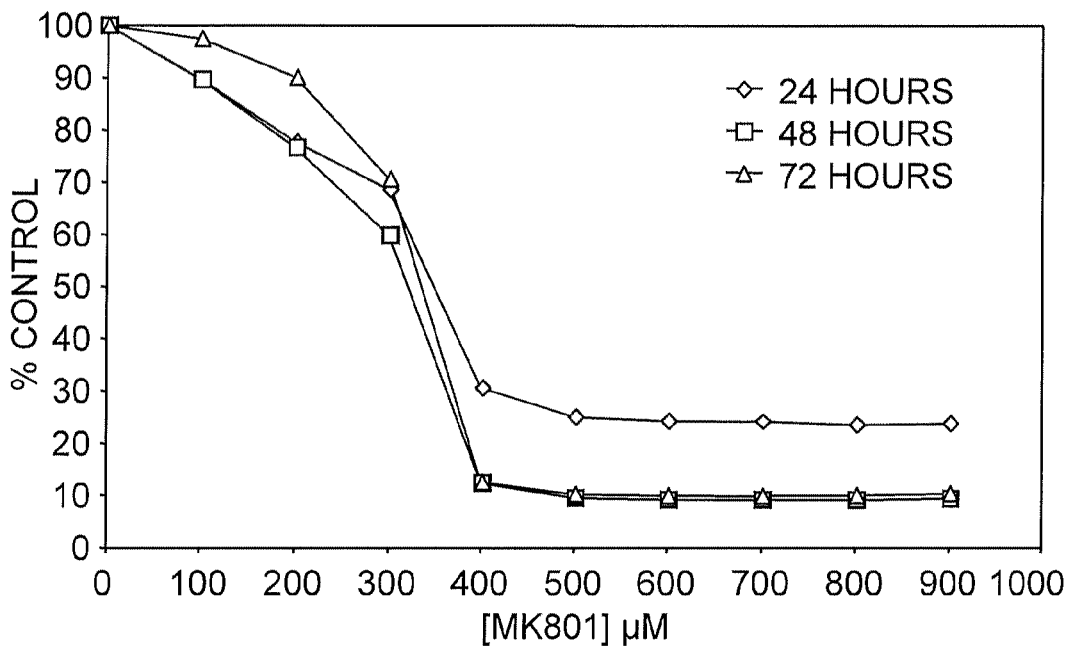
FIG. 2B shows the percentage reduction in cell viability produced in NCI-H82 variant cells by the action of irreversible NMDAR1 receptor antagonist MK-801 following 24, 48, and 72 hours incubation. Cell viability was reduced to about 10% of control and assessed using Alamar Blue staining. Reductions in viability were highly significant ($p<0.0001$) and $IC_{50}$s were obtained with ~200 µM doses of antagonist at 48 and 72 hours of incubation.
Figure 3A:
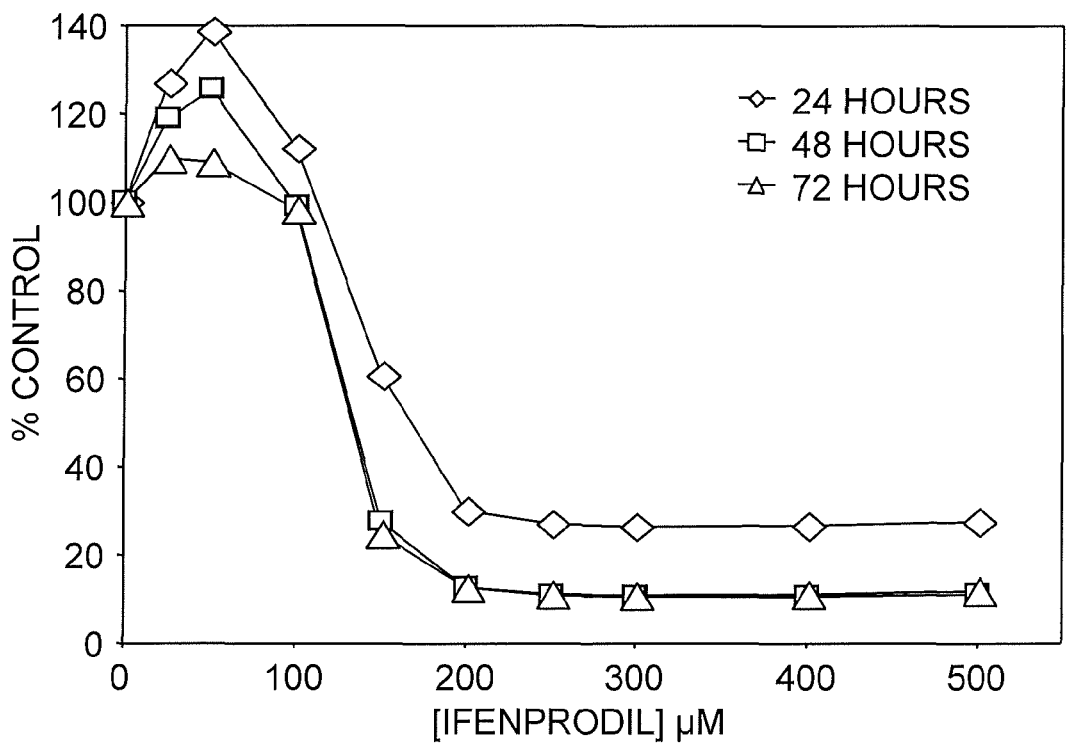
FIG. 3A shows the percentage reduction in cell viability produced in NCI-H345 classical cells by the action of irreversible NMDAR2B receptor antagonist Ifenprodil following 24, 48, and 72 hours incubation.
Figure 3B:
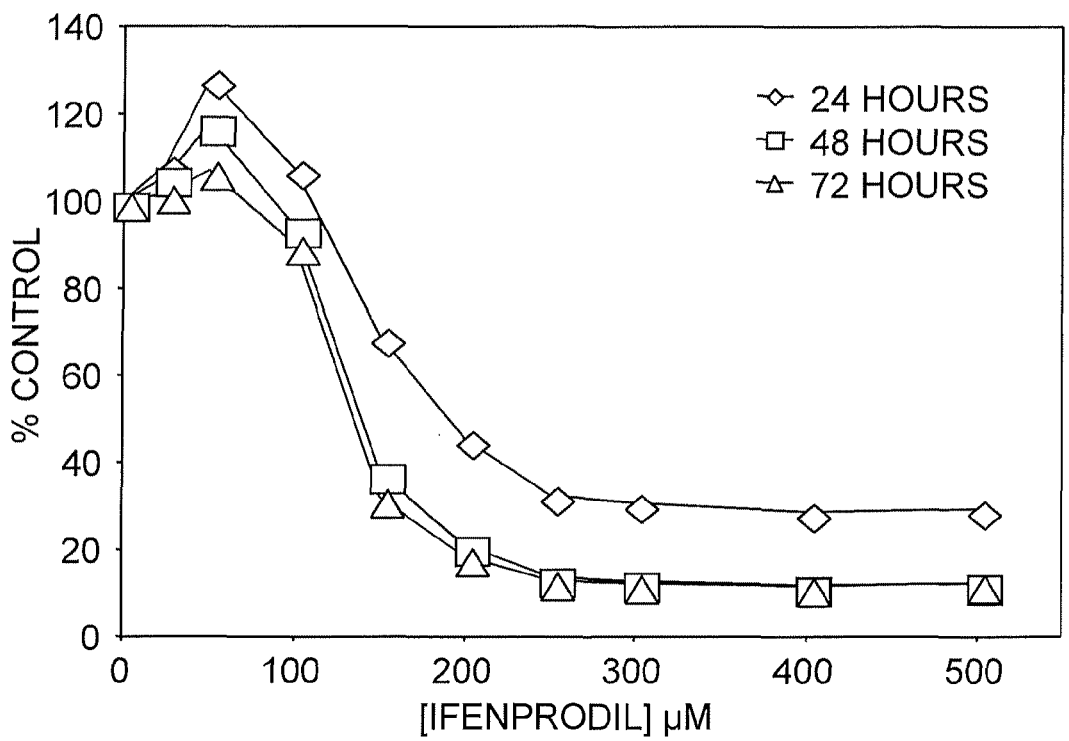
FIG. 3B shows the percentage reduction in cell viability produced in NCI-H82 variant cells by the action of irreversible NMDAR2B receptor antagonist Ifenprodil following 24, 48, and 72 hours incubation. Cell viability was reduced to about 10% of control and assessed using Alamar Blue staining. Reductions in viability were highly significant ($p<0.0001$) and $IC_{50}$s were obtained with 150-200 µM doses of antagonist at 48 and 72 hours of incubation.

NMDAR antagonist activity on the viability of small-cell cancer cells was also analyzed. Significant effects (p<0.01) on cell viability by different antagonists (reductions to 10% control or increases to 140% control) were found at all three incubation times of 24, 48, and 72 hours. The changes induced following 48 hours and 72 hours of incubation were similar, and greater than those found following 24 hours of incubation. Effects were also different for the different cell lines. Memantine and MK-801 produced dramatic decreases (p<0.0001) in cell viability (FIGS. 1 and 2), with $IC_{50}$s at 48 hours of 80-130 μM for NCI-H345 and NCI-H82, 400 μM for NCI-H146, and 800 μM for DMS-53 cells with memantine; and of 300 μM for NCI-H345 and NCI-H82, 650 μM for NCI-H146, and >800 μM for DMS-53 with MK-801. Both Ifenprodil and Ro 25-6981 also decreased cell viability (FIG. 3) with respective $IC_{50}$s at 48 hours of ~150 and ~200 μM for both NCI-H345 and NCI-H82 cells, but a reduction no greater than 40% with NCI-H146, and smaller decreases with DMS-53 with Ifenprodil, and no clear effects at the concentration range used with Ro 25-698. The effects of the glycine site binders were only examined on NCI-H345 and NCI-H82. At 48 hours, L-701,324 produced an increase in cell viability to approximately 140% and 120% of control for NCI-H345 and NCI-H82, respectively. At 48 hours, L-701,252 also produced an increase to approximately 120% of control for NCI-H345 cells, but no clear effect over the concentration range for NCI-H82 cells. Differences were observed in these studies between different cell lines and these differences probably reflect either a concentration range of NMDARs or a differing dependence of the cells on functional NMDARs for growth. However, effects were greatest on the one variant cell line (and one classical cell line) and this variant cell line represents recurrent and drug-resistant disease. Moreover, it is of interest that preventing glycine from binding to NMDAR1 receptors seemed to improve cell survival.

The ability of an NMDAR1 antibody to inhibit tumor cell growth was also demonstrated. An affinity-purified preparation of PENN1 (anti-NMDAR1) rabbit polyclonal antibodies was incubated with small cell lung cancer NCI-H345 cells for 24 hours at 1:50 (<<10 ng, <75 fmol antibody) or 1:10 (<<50 ng, <0.375 fmol antibody). The results of this analysis indicated that the antibody significantly (P<0.001) decreased the proliferation of small cell lung cancer NCI-H345 cells in culture by about 6% and 25%, respectively, compared to controls (Table 6).

TABLE 6

| Treatment (24 Hour) | Fluorescence of Alamar Blue |
|---|---|
| Control, 1:50 | 723.5 ± 3.8 |
| AntiNMDAR1, 1:50 | 678.0 ± 2.8** |
| Control, 1:10 | 811.3 ± 5.5 |
| AntiNMDAR1, 1:10 | 617.0 ± 2.9** |

*Significant at p < 0.001 compared with control

These data showed an importance of NMDAR1 receptors in the proliferation of this SCLC cell line, and demonstrated the availability of the antigenic site on the receptors for antibody binding, wherein such binding disrupts signaling through these channels. Additionally, the data indicates that increased doses of the PENN1 antibody or similar antibodies, especially directing cell cytotoxicity in vitro and in vivo, could kill most, or all such cancer cells. Because antigenic sequences of human NMDAR1 protein and mouse NMDAR1 protein are identical, mice are suitable models to study the effects of anti-NMDAR1s on tumors in vivo.

Figure 4:
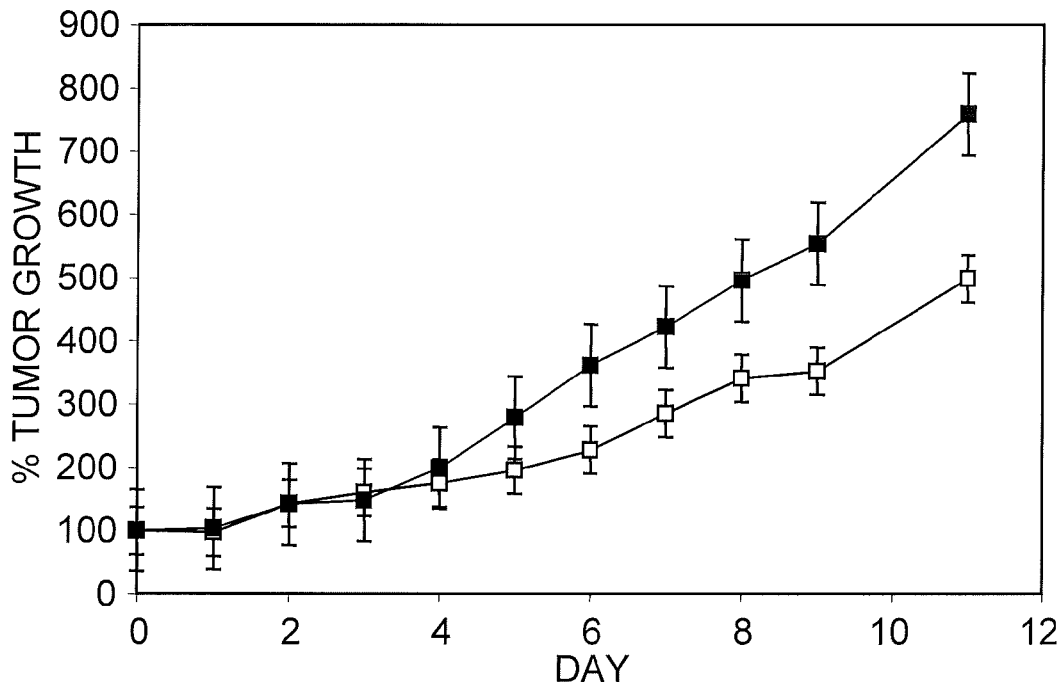
FIG. 4 shows the inhibition of SCLC NCI-H345 tumors in control (closed symbol) and treated (open symbol) animals. Growth of small-cell tumors from NCI-H345 cells was significantly ($p<0.0001$) reduced by treatment with escalating doses of MK-801 from 0.1 mg/kg once daily to 0.3 mg/kg given twice daily as indicated. Tumor volume measured by micrometer was expressed as the product of length×width×breadth and was evaluated on a daily basis.

Accordingly, NMDAR antagonism was monitored in vivo in a mouse tumor model. The treatment of established human small-cell tumor xenografts in nu/nu mice with MK-801, at the dose indicated herein, produced no noticeable behavioral effects in the animals and had no apparent effect on their well-being as exemplified by body weight in treated animals paralleling that for controls. However, as shown in FIG. 4, MK-801 produced highly significant (p<0.001) reductions in the rate of tumor growth, to almost 60% that of controls, over the course of the study. This effect on growth was evident for even the lowest dose used, i.e., 0.1 mg/Kg body weight.

Figure 5:
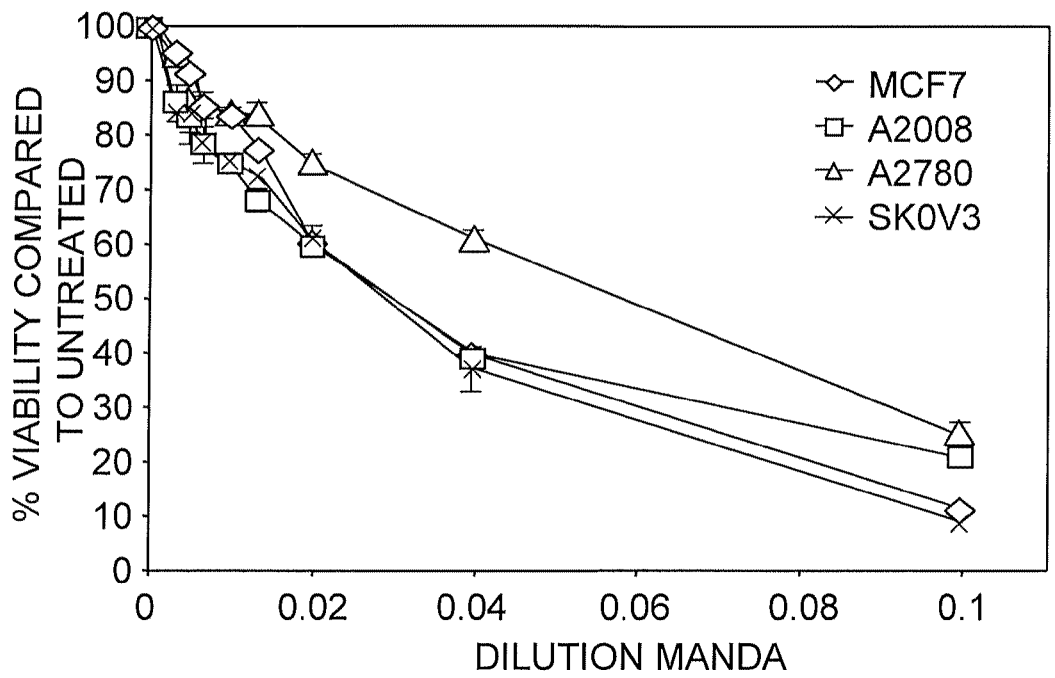
FIG. 5 shows the influence of MK-801 and anti-NMDAR on ovarian cancer cell proliferation.

Ovarian Cancer. Ovarian A2780 and A2008 cancer cells were plated in 96 well plates at $1-2\times10^4$ cells/well. The cells were incubated with PBS/glycine containing albumin (1.25 mg/ml), in the presence of differing concentrations of NMDA antagonist MK-801, different dilutions of IgG isolated Manda anti-NMDAR1 polyclonal antibodies, or vehicle. Alamar Blue was later added to each well following an incubation period, and fluorescent readings taken at excitation 530-560 nm and emission of 590 nm and above on a SYNERGY HT Multi Detection Reader. MK-801 and anti-NMDAR1 antibodies produced dramatic reductions in cell growth; more than 50% reduction in fluorescent units at 500, 600, 700, 800, and 900 µM compared to 100, 200 and 400 µM. Significance was p<0.001 for 400 to 900 µM of MK-801. Nanogram quantities of anti-NMDAR antibodies were also able to considerably inhibit growth (FIG. 5). These findings indicate both NMDAR antagonists and anti-NMDA receptor monoclonal antibodies would be of use as effective inhibitors of ovarian tumor xenografts in mice. It is of note that similar amounts of MK-801 and antibody had the same effects on human breast cancer cells and completely inhibited growth of these tumors in vivo.

Figure 6:
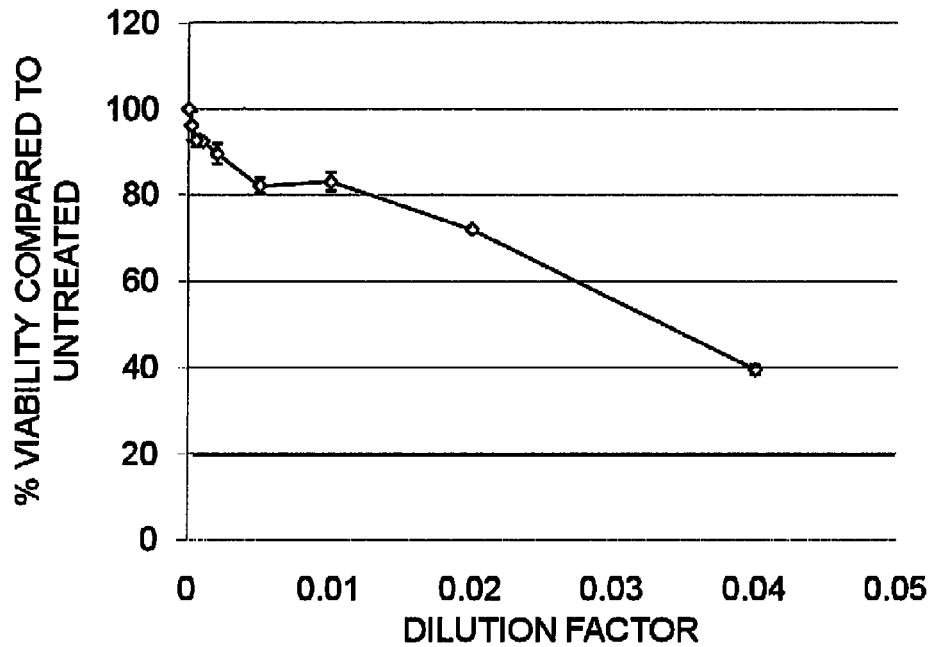
FIG. 6 shows a decrease in viability of LNCAP prostate cancer cells with anti-NMDAR antibodies.

Prostate Cancer. To determine the effects of NMDAR1 antibodies on prostate cell viability, LNCAP prostate cancer cells were plated in 96 well plates at $1-2\times10^4$ cells/well. The cells were incubated with PBS/glycine containing albumin (1.25 mg/ml), in the presence of differing concentrations of different dilutions of IgG isolated Manda anti-NMDAR1 polyclonal antibodies, or MK801, or vehicle. Alamar Blue was later added to each well following an incubation period, and fluorescent readings taken at excitation 530-560 nm and emission 590 nm and above on a SYNERGY HT Multi Detection Reader. Nanogram quantities of anti-NMDAR1 antibodies produced dramatic and highly significant reductions in cell growth (FIG. 6). Also, significance in reductions was p<0.001 for 400 to 900 µM of MK-801.

Figure 7A:
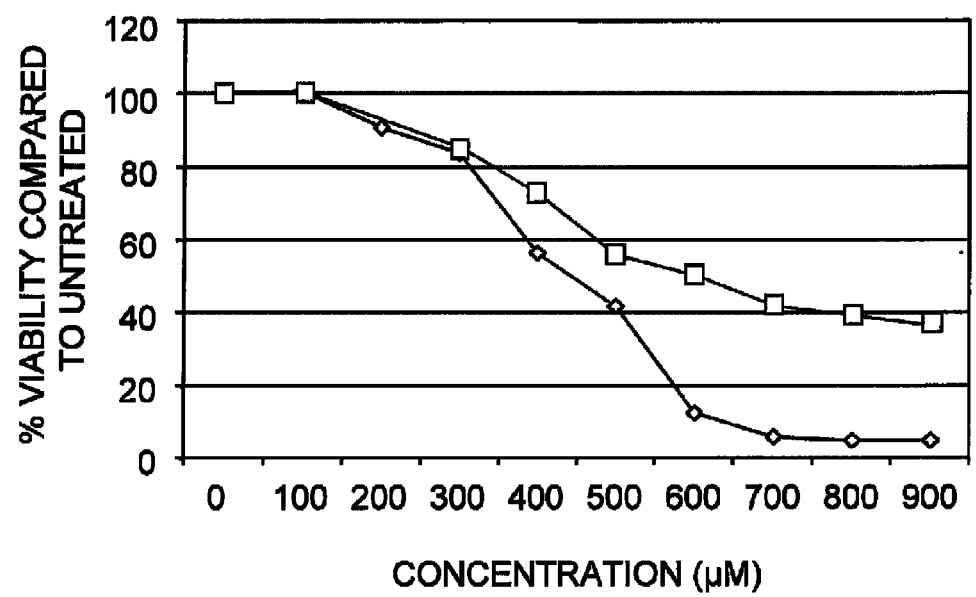
FIG. 7 shows the influence of MK-801 (FIG. 7A) and anti-NMDAR antibody (Manda, FIG. 7B) on the proliferation of pancreatic cancer cells.
Figure 7B:
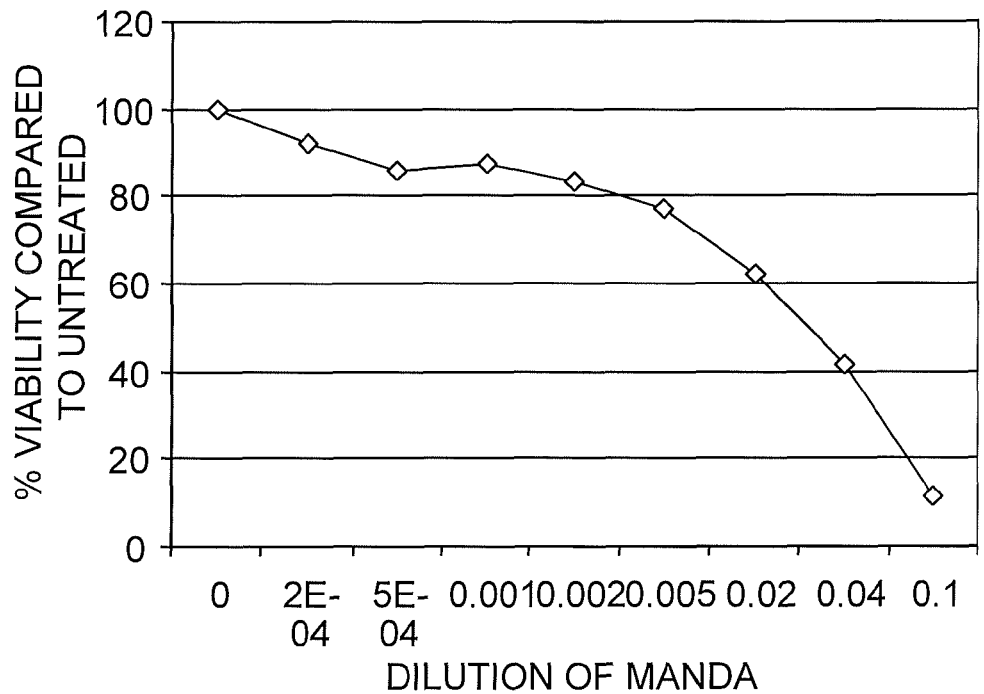

Pancreatic Cancer. Pancreatic HPAC-1 and BXCPC-3 cancer cells were plated in 96-well plates at $1-2\times10^4$ cells/well. The cells were incubated with PBS/glycine containing albumin (1.25 mg/ml), in the presence of differing concentrations of NMDA antagonist MK-801 (FIG. 7A), different dilutions of IgG-isolated Manda anti-NMDAR1 polyclonal antibody (FIG. 7B), or vehicle. Alamar Blue was later added to each well following an incubation period, and fluorescent readings taken at excitation 530-560 nm and emission 590 nm and above on a SYNERGY HT Multi Detection Reader. MK-801 and anti-NMDAR1 antibodies produced dramatic reductions in cell growth. Significance was p<0.001 for 200 to 600 µM of MK-801. Nanogram quantities of anti-NMDAR antibodies were also able to considerably inhibit growth. These findings indicate that both NMDAR antagonists and anti-NMDA receptor antibodies would be effective inhibitors of pancreatic tumor xenografts in mice.

Example 4

In Vivo Anti-Cancer Activity of NMDAR Antagonists

Figure 8:
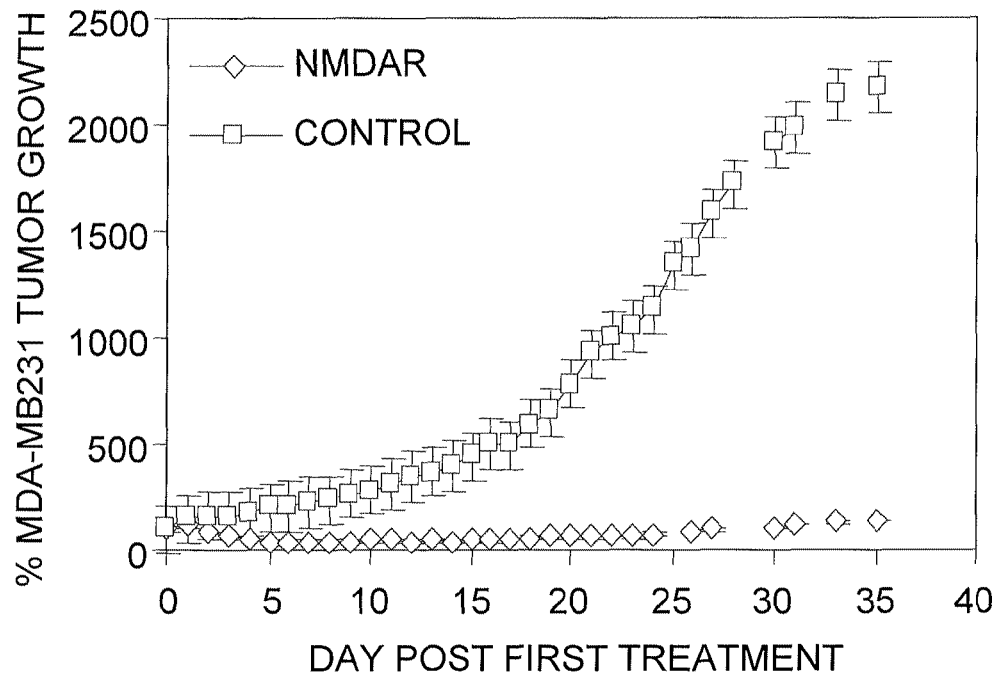
FIG. 8 shows inhibition of cancer growth in mice with polyclonal antibodies (Day 0 set 100%).

Human tumor xenografts of breast cancer cells were raised in nu/nu mice, and the influence of anti-NMDAR1 polyclonal antibodies then examined on tumor growth. For antibody studies, growth in a control group (n=4) was compared to tumor growth in animals (n=4) receiving 50 ng of Protein A-isolated, antibody-containing, IgG once each day for 15 days. Tumor was then measured for an additional days. While control tumors grew to >20 times their original size, tumors treated with anti-NMDAR1 antibodies shrank to <50% original size and remained at this shrunken size for the duration of treatment (p<<0.0001) (FIG. 8). Tumor size then began very slowly to rise but even 20 days later they were only back to original size (100%). Values are expressed as a percentage of tumor size at day 0 (+/−SEM). The dosing of antibodies produced no noticeable behavioral effects in the animals and had no apparent effect on their well-being as exemplified by daily body weights in treated animals paralleling those for controls. For antibody treatment, H&E stained liver, kidney, and brain showed no differences between treated and control animals at 36 days. Treated tumors displayed >50% necrosis. These results indicate that anti-NMDAR1 antibodies are safe and effective as imaging and treatment agents for breast cancer as well as other neuroendocrine cancers.

What is claimed is:

1. A method for diagnosing pancreatic cancer in a patient comprising isolating a pancreatic tissue sample from a patient suspected of having pancreatic cancer, contacting said pancreatic tissue sample with a binding agent capable of detecting a level of NMDA-1 glutamate receptor protein in said sample, contacting a pancreatic tissue sample known to be free of pancreatic cancer with said binding agent, comparing the levels of NMDA-1 glutamate receptor protein in the pancreatic tissue samples, and diagnosing pancreatic cancer in the patient, wherein an increase in the level of NMDA-1 glutamate receptor protein in the sample from the patient suspected of having pancreatic cancer as compared to the level detected in the pancreatic tissue sample known to be free of pancreatic cancer indicates the patient has pancreatic cancer.

* * * * *

SEQUENCE LISTING

```
<160> NUMBER OF SEQ ID NOS: 11

<210> SEQ ID NO 1
<211> LENGTH: 22
<212> TYPE: DNA
<213> ORGANISM: Artificial sequence
<220> FEATURE:
<223> OTHER INFORMATION: Synthetic primer

<400> SEQUENCE: 1
```

-continued atctactcgg acaagagcat cc                                    22

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
agctctttcg cctccatcag                                       20

<210> SEQ ID NO 3
<211> LENGTH: 21
<212> TYPE: DNA
<213> ORGANISM: Artificial sequence
<220> FEATURE:
<223> OTHER INFORMATION: Synthetic primer

<400> SEQUENCE: 3
aagtatgcgg atggggtgac t                                     21

<210> SEQ ID NO 4
<211> LENGTH: 21
<212> TYPE: DNA
<213> ORGANISM: Artificial sequence
<220> FEATURE:
<223> OTHER INFORMATION: Synthetic primer

<400> SEQUENCE: 4
caaaagccgt agcaacactg a                                     21

<210> SEQ ID NO 5
<211> LENGTH: 10
<212> TYPE: PRT
<213> ORGANISM: Artificial sequence
<220> FEATURE:
<223> OTHER INFORMATION: Synthetic peptide

<400> SEQUENCE: 5

Met Ser Ile Tyr Ser Asp Lys Ser Ile His
1               5                   10

<210> SEQ ID NO 6
<211> LENGTH: 21
<212> TYPE: DNA
<213> ORGANISM: Artificial sequence
<220> FEATURE:
<223> OTHER INFORMATION: Synthetic primer

<400> SEQUENCE: 6
tcaaggatgc ccacgagaaa g                                     21

<210> SEQ ID NO 7
<211> LENGTH: 21
<212> TYPE: DNA
<213> ORGANISM: Artificial sequence
<220> FEATURE:
<223> OTHER INFORMATION: Synthetic primer

<400> SEQUENCE: 7
gtggcttctt ccttgtgaca g                                     21

<210> SEQ ID NO 8
<211> LENGTH: 19
<212> TYPE: DNA
<213> ORGANISM: Artificial sequence

```
-continued

<220> FEATURE:
<223> OTHER INFORMATION: Synthetic primer

<400> SEQUENCE: 8
ccaaagagca tcatcaccc                                                19

<210> SEQ ID NO 9
<211> LENGTH: 19
<212> TYPE: DNA
<213> ORGANISM: Artificial sequence
<220> FEATURE:
<223> OTHER INFORMATION: Synthetic primer

<400> SEQUENCE: 9
tgtagccata gccagtcag                                                19

<210> SEQ ID NO 10
<211> LENGTH: 20
<212> TYPE: DNA
<213> ORGANISM: Artificial sequence
<220> FEATURE:
<223> OTHER INFORMATION: Synthetic primer

<400> SEQUENCE: 10
tccaatagtg ccctgctaag                                               20

<210> SEQ ID NO 11
<211> LENGTH: 20
<212> TYPE: DNA
<213> ORGANISM: Artificial sequence
<220> FEATURE:
<223> OTHER INFORMATION: Synthetic primer

<400> SEQUENCE: 11
tgccaacata cccagtaggc                                               20
```